United States Patent
Prasad et al.

(10) Patent No.: US 12,105,093 B2
(45) Date of Patent: Oct. 1, 2024

(54) QUANTITATION OF GLA PROTEINS BY MASS SPECTROMETRIC ANALYSIS

(71) Applicants: University of Washington, Seattle, WA (US); Washington State University, Pullman, WA (US)

(72) Inventors: Bhagwat Prasad, Seattle, WA (US); Kenneth E. Thummel, Seattle, WA (US); Abdul Basit Shaikh, Seattle, WA (US); Allan E. Rettie, Seattle, WA (US)

(73) Assignees: University of Washington, Seattle, WA (US); Washington State University, Pullman, WA (US)

( * ) Notice: Subject to any disclaimer, the term of this patent is extended or adjusted under 35 U.S.C. 154(b) by 206 days.

(21) Appl. No.: 17/386,234

(22) Filed: Jul. 27, 2021

(65) Prior Publication Data

US 2022/0034901 A1 Feb. 3, 2022

Related U.S. Application Data

(60) Provisional application No. 63/057,730, filed on Jul. 28, 2020.

(51) Int. Cl.
*G01N 33/68* (2006.01)
(52) U.S. Cl.
CPC .............................. *G01N 33/6848* (2013.01)
(58) Field of Classification Search
None
See application file for complete search history.

(56) References Cited

U.S. PATENT DOCUMENTS

2018/0284119 A1  10/2018  Kitamura
2019/0383830 A1  12/2019  Sin

FOREIGN PATENT DOCUMENTS

| CN | 103837593 A | 6/2014 |
|---|---|---|
| CN | 106770872 A | 5/2017 |
| CN | 109425740 A | 3/2019 |
| CN | 109444422 A | 3/2019 |
| EP | 1766412 B1 | 4/2009 |
| KR | 101796874 B1 | 11/2017 |
| WO | 2007044935 A2 | 4/2007 |
| WO | 2015074048 A1 | 5/2015 |
| WO | 2016118489 A1 | 7/2016 |

OTHER PUBLICATIONS

Agarwal S, Hachamovitch R, Menon V. Current trial-associated outcomes with warfarin in prevention of stroke in patients with nonvalvular atrial fibrillation: A meta-analysis. Arch Intern Med 2012;172:623-31; discussion 31-3.

(Continued)

*Primary Examiner* — Xiaoyun R Xu
(74) *Attorney, Agent, or Firm* — Christensen O'Connor Johnson Kindness PLLC

(57) ABSTRACT

Methods of LC-MS/MS quantification of γ-carboxylated proteins in plasma, serum, or blood, including dried blood spots, are disclosed. The methods can be used to determine patient-specific dosing of anticoagulant drugs and diagnosis of liver diseases, such as hepatocellular carcinoma.

15 Claims, 20 Drawing Sheets

Specification includes a Sequence Listing.

(56) References Cited

OTHER PUBLICATIONS

Basit, A. et al. A novel LC-MS/MS method for PIVKAII quantification: Characterization of warfarin induced altered prothrombin des-carboxylation. International Society for the Study of Xenobiotics 12th International Meeting. Portland, Oregon. Jul. 29, 2019.

Basit, A. et al. A Novel LC-MS/MS Assay for Quantification of Des-carboxy Prothrombin and Characterization of Warfarin-Induced Changes. Clinical and Translational Science. vol. 13, issue 4, Jul. 2020, 718-726.

Basit, A. et al. LC-MS/MS assay for vitamin K dependent γ-carboxylated proteins: (FII, FVII, FIX, FX, Protein C, Protein S and Protein Z). Pharmacogenomics Global Research Network Meeting. Jan. 15, 2020.

Bellei E, Bergamini S, Monari E, Fantoni LI, Cuoghi A, Ozben T, Tomasi A. High-abundance proteins depletion for serum proteomic analysis: Concomitant removal of non-targeted proteins. Amino Acids 2011;40:145-56.

Bhatt DK, Prasad B. Critical issues and optimized practices in quantification of protein abundance level to determine interindividual variability in dmet proteins by lc-ms/ms proteomics. Clin Pharmacol Ther 2018;103:619-30.

Chernonosov, A. Quantification of Warfarin in Dried Rat Plasma Spots by High-Performance Liquid Chromatography with Tandem Mass Spectrometry. Journal of Pharmaceutics. vol. 2016, Article ID 6053295.

Costa IM, Soares PJ, Afonso M, Ratado P, Lanaot JM, Falcao AC. Therapeutic monitoring of warfarin: The appropriate response marker. J Pharm Pharmacol 2000;52:1405-10.

Cove CL, Hylek EM. An updated review of target-specific oral anticoagulants used in stroke prevention in atrial fibrillation, venous thromboembolic disease, and acute coronary syndromes. J Am Heart Assoc 2013;2:e000136.

Cropp JS, Bussey HI. A review of enzyme induction of warfarin metabolism with recommendations for patient management. Pharmacotherapy 1997;17:917-28.

Daly AK, Rettie AE, Fowler DM, Miners JO. Pharmacogenomics of cyp2c9: Functional and clinical considerations. J Pers Med 2018;8,1.

Dituri F, Buonocore G, Pietravalle A, Naddeo F, Cortesi M, Pasqualetti P, et al. Pivka-ii plasma levels as markers of subclinical vitamin k deficiency in term infants. J Matern Fetal Neonatal Med 2012;25:1660-3.

Doneanu, C. et al. Analysis of host-cell proteins in biotherapeutic proteins by comprehensive online two-dimensional liquid chromatography/mass spectrometry. mAbs. vol. 4, issue 1, 2012, 24-44.

Flora DR, Rettie AE, Brundage RC, Tracy TS. Cyp2c9 genotype-dependent warfarin pharmacokinetics: Impact of cyp2c9 genotype on r-and s-warfarin and their oxidative metabolites. J Clin Pharmacol 2017;57(3):382-93.

Fohner AE, Robinson R, Yracheta J, Dillard DA, Schilling B, Khan B, et al. Variation in genes controlling warfarin disposition and response in american indian and alaska native people: Cyp2c9, vkorc1, cyp4f2, cyp4f11, ggcx. Pharmacogenet Genomics 2015;25(7):343-53.

Fujita, K. et al. Development and evaluation of analytical performance of a fully automated chemiluminescent immunoassay for protein induced by vitamin K absence or antagonist II. Clinical Biochemistry. vol. 48, issue 18. Dec. 2015, pp. 1330-1336.

Fujiyama S, Morishita T, Shibata J, Sato T. Clinical usefulness of plasma PIVKA-II assay and its limitations in patients with hepatocellular carcinoma. Gan To Kagaku Ryoho/Japanese Journal of Cancer and Chemotherapy. 1989;16(4):1129-1138.

Hallgren KW, Zhang D, Kinter M, Willard B, Berkner KL. Methylation of gamma-carboxylated glu (gla) allows detection by liquid chromatography-mass spectrometry and the identification of gla residues in the gamma-glutamyl carboxylase. J Proteome Res 2013;12:2365-2374.

Henderson LM, Robinson RF, Ray L, Khan BA, Li T, Dillard DA, et al. Vkorc1 and novel cyp2c9 variation predict warfarin response in alaska native and american indian people. Clin Transl Sci 2019;12:312-20.

Holbrook AM, Pereira JA, Labiris R, McDonald H, Douketis JD, Crowther M, Wells PS. Systematic overview of warfarin and its drug and food interactions. Arch Intern Med 2005;165:1095-106.

Hylek EM, Singer DE. Risk factors for intracranial hemorrhage in outpatients taking warfarin. Ann Intern Med 1994;120:897-902.

Jeong, H.-C. et al. Quantification of apixaban in human plasma using ultra performance liquid chromatography coupled with tandem mass spectrometry. Transl Clin Pharmacol. Mar. 2019;27(1):33-41.

Katz JJ. Anhydrous trifluoroacetic acid as a solvent for proteins. Nature. Sep. 11, 1954;174(4428):509.

Keshishian H, Burgess MW, Gillette MA, Mertins P, Clauser KR, Mani DR, et al. Multiplexed, quantitative workflow for sensitive biomarker discovery in plasma yields novel candidates for early myocardial injury. Mol Cell Proteomics 2015;14:2375-93.

Kuromatsu, R. et al. Usefulness of ED036 kit for measuring serum PIVKA-II levels in small hepatocellular carcinoma. Journal of Gastroenterology. 32 (1997) 507.

Kuruvilla M, Gurk-Turner C. A review of warfarin dosing and monitoring. Proc (Bayl Univ Med Cent) 2001;14:305-6.

Lamerz R, Runge M, Stieber P, Meissner E. Use of serum pivka-ii (dcp) determination for differentiation between benign and malignant liver diseases. Anticancer Res 1999;19:2489-93.

Langoutte-Renosi et al. A simple and fast HPLC-MS/MS method for simultaneous determination of direct oral anticoagulants apixaban, dabigatran, rivaroxaban in human plasma. Journal of Chromatohraphy B. vols. 1100-1101, Nov. 15, 2018, 43-49.

Lee SE, West KP, Jr., Cole RN, Schulze KJ, Christian P, Wu LS, et al. Plasma proteome biomarkers of inflammation in school aged children in nepal. PLoS One 2015;10:e0144279.

Liu G, Zhao Y, Angeles A, Hamuro LL, Arnold ME, Shen JX. A novel and cost effective method of removing excess albumin from plasma/serum samples and its impacts on lc-ms/ms bioanalysis of therapeutic proteins. Anal Chem 2014;86:8336-43.

Makris, M. et al. Warfarin anticoagulation reversal: management of the asymptomatic and bleeding patient. J Thromb Thrombolysis (2010) 29:171-181.

Malhotra OP, Nesheim ME, Mann KG. The kinetics of activation of normal and gamma-carboxyglutamic acid-deficient prothrombins. J Biol Chem 1985;260(1):279-87.

Marrero JA, Su GL, Wei W, Emick D, Conjeevaram HS, Fontana RJ, Lok AS. Des-gamma carboxyprothrombin can differentiate hepatocellular carcinoma from nonmalignant chronic liver disease in american patients. Hepatology 2003;37(5):1114-21.

Martel, J. et al. Comprehensive proteomic analysis of mineral nanoparticles derived from human body fluids and analyzed by liquid chromatography-tandem mass spectrometry. Analytical Biochemistry. vol. 418, issue 1, Nov. 1, 2011, 111-125.

McDonald MG, Yeung CK, Teitelbaum AM, Johnson AL, Fujii S, Kagechika H, Rettie AE. A new lc-ms assay for the quantitative analysis of vitamin k metabolites in human urine. J Lipid Res 2019;60:892-9.

Meguro, T. et al. A simple and rapid test for Pivka-II in plasma. Thrombosis Research. vol. 25, issue 1-2, 1982, 109-114.

Naryzhny, S. et al. Variety and Dynamics of Proteoforms in the Human Proteome: Aspects of Markers for Hepatocellular Carcinoma. Proteomes. 5(4) 2017, 33.

Percy, A.J. et al. A standardized kit for automated quantitative assessment of candidate protein biomarkers in human plasma. Bioanalysis. vol. 7, No. 23, Dec. 2, 2015, pp. 2991-3004.

Qian, W.-J. et al. Comparative proteome analyses of human plasma following in vivo lipopolysaccharide administration using multidimensional separations coupled with tandem mass spectrometry. Proteomics. vol. 5, issue 2, Feb. 8, 2005, pp. 572-584.

Ratcliffe JV, Furie B, Furie BC. The importance of specific gamma-carboxyglutamic acid residues in prothrombin. Evaluation by site-specific mutagenesis. J Biol Chem 1993;268(32):24339-45.

(56) References Cited

OTHER PUBLICATIONS

Rice, S.J. et al. Absolute Quantification of All Identified Plasma Proteins from SWATH Data for Biomarker Discovery. Proteomics. 2019. vol. 19, issue 3, p. 1800135.

Rohde LE, de Assis MC, Rabelo ER. Dietary vitamin k intake and anticoagulation in elderly patients. Curr Opin Clin Nutr Metab Care 2007;10:1-5.

Ryu, M.R. et al. Performance evaluation of serum PIVKA-II measurement using HISCL-5000 and a method comparison of HISCL-5000, Lumipulse G1200, and Architect i2000. Journal of Clinical Laboratory Analysis. vol. 33, issue 6, Jul. 2019, e22921.

Saghir SAM, Al-Hassan FM, Alsalahi OS, Abdul Manaf FS, Baqir HS. Optimization of the storage conditions for coagulation screening tests. J Coll Physicians Surg Pak 2012;22(5):294-7.

Saitoh, S. et al. Serum des-gamma-carboxyprothrombin concentration determined by the avidin-biotin complex method in small hepatocellular carcinomas. Cancer. vol. 74, Issue 11, 1994, 2918-2923.

Schmitz, E.M.H. et al. Determination of dabigatran, rivaroxaban and apixaban by ultra-performance liquid chromatography—tandem mass spectrometry (UPLC-MS/MS) and coagulation assays for therapy monitoring of novel direct oral anticoagulants. Journal of Thrombosis and Haemostasis. vol. 12, issue 10, Aug. 20, 2014, 1636-1646.

Shi, T. et al. Advancing the sensitivity of selected reaction monitoring-based targeted quantitative proteomics. Proteomics. Apr. 2012; 12(8): 1074-1092.

Sohn A, Kim H, Yeo I, Kim Y, Son M, Yu SJ, et al. Fully validated srm-ms-based method for absolute quantification of pivka-ii in human serum: Clinical applications for patients with HCC. J Pharm Biomed Anal 2018;156:142-6.

Sohn A, Kim H, Yu SJ, Yoon JH, Kim Y. A quantitative analytical method for pivka-ii using multiple reaction monitoring-mass spectrometry for early diagnosis of hepatocellular carcinoma. Anal Bioanal Chem 2017;409:2829-38.

Tie JK, Carneiro JD, Jin DY, Martinhago CD, Vermeer C, Stafford DW. Characterization of vitamin k-dependent carboxylase mutations that cause bleeding and nonbleeding disorders. Blood 2016;127(15):1847-55.

Toyoda H, Kumada T, Osaki Y, Tada T, Kaneoka Y, Maeda A. Novel method to measure serum levels of des-gamma-carboxy prothrombin for hepatocellular carcinoma in patients taking warfarin: A preliminary report. Cancer Sci 2012;103(5):921-5.

Tsai, T.-H. et al. LC-MS/MS-based serum proteomics for identification of candidate biomarkers for hepatocellular carcinoma. Proteomics. vol. 15, issue 13, Jul. 2015, 2369-2381.

Tu C, Rudnick PA, Martinez MY, Cheek KL, Stein SE, Slebos RJ, Liebler DC. Depletion of abundant plasma proteins and limitations of plasma proteomics. J Proteome Res 2010;9:4982-91.

Uehara S, Gotoh K, Handa H, Honjo K, Hirayama A. Process of carboxylation of glutamic acid residues in the gla domain of human des-gamma-carboxyprothrombin. Clin Chim Acta 1999;289:33-44.

Van Geest-Daalderop JH, Mulder AB, Boonman-de Winter LJ, Hoekstra MM, van den Besselaar AM. Preanalytical variables and off-site blood collection: Influences on the results of the prothrombin time/international normalized ratio test and implications for monitoring of oral anticoagulant therapy. Clin Chem 2005;51:561-8.

Weinstock, D.M. et al. Comparison of Plasma Prothrombin and Factor VII and Urine Prothrombin F1 Concentrations in Patients on Long-Term Warfarin Therapy and Those in the Initial Phase. American Journal of Hematology. 57:193-199 (1998).

Witt, D.M. et al. Guidance for the practical management of warfarin therapy in the treatment of venous thromboembolism. J Thromb Thrombolysis. 2016; 41: 187-205.

Yu R, Ding S, Tan W, Tan S, Tan Z, Xiang S, et al. Performance of protein induced by vitamin k absence or antagonist-ii (pivka-ii) for hepatocellular carcinoma screening in chinese population. Hepat Mon Jul. 2015;15(7): e28806.

Yu R, Tan Z, Xiang X, Dan Y, Deng G. Effectiveness of pivka-ii in the detection of hepatocellular carcinoma based on real-world clinical data. BMC Cancer 2017;17:608.

Zakhary NI, Khodeer SM, Shafik HE, Abdel Malak CA. Impact of pivka-ii in diagnosis of hepatocellular carcinoma. J Adv Res 2013;4:539-46.

Zhang, H. et al. High Throughput Quantitative Analysis of Serum Proteins Using Glycopeptide Capture and Liquid Chromatography Mass Spectrometry. Molecular & Cellular Proteomics. vol. 4, issue 2, Feb. 1, 2005, 144-155.

Zhang, J.E. et al. Effect of Genetic Variability in the CYP4F2, CYP4F11, and CYP4F12 Genes on Liver mRNA Levels and Warfarin Response. Frontiers in Pharmacology. vol. 8. Article 323, May 2017.

SEQUENCE LISTING

<160> NUMBER OF SEQ ID NOS: 77

<210> SEQ ID NO 1
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as gamma-
      carboxylated glutamic acid
<220> FEATURE:
<221> NAME/KEY: MISC_FEATURE
<222> LOCATION: (7)..(7)

```
<223> OTHER INFORMATION: Wherein X at position 7 is defined as gamma-
      carboxylated glutamic acid

<400> SEQUENCE: 1

Ala Asn Ser Phe Leu Xaa Xaa Met Lys
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as E-(CH3)2
      (derivatized gamma-carboxylated glutamic acid)
<220> FEATURE:
<221> NAME/KEY: MISC_FEATURE
<222> LOCATION: (7)..(7)
<223> OTHER INFORMATION: Wherein X at position 7 is defined as E-(CH3)2
      (derivatized gamma-carboxylated glutamic acid)
<220> FEATURE:
<221> NAME/KEY: MISC_FEATURE
<222> LOCATION: (9)..(9)
<223> OTHER INFORMATION: Wherein X at position 9 is defined as K-CH3
      (derivatized carboxyl terminal lysine)

<400> SEQUENCE: 2

Ala Asn Ser Phe Leu Xaa Xaa Met Xaa
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic

<400> SEQUENCE: 3

Ala Asn Thr Phe Leu Glu Glu Val Arg Lys
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid

<400> SEQUENCE: 4

Ala Asn Thr Phe Leu Glu Xaa Val Arg Lys
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as gamma-
      carboxylated glutamic acid
```

```
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid

<400> SEQUENCE: 5

Ala Asn Thr Phe Leu Xaa Xaa Val Arg Lys
1               5                   10

<210> SEQ ID NO 6
<211> LENGTH: 5
<212> TYPE: PRT
<213> ORGANISM: Artificial sequence
<220> FEATURE:
<223> OTHER INFORMATION: Synthetic

<400> SEQUENCE: 6

Gly Asn Leu Glu Arg
1               5

<210> SEQ ID NO 7
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Wherein X at position 4 is defined as gamma-
      carboxylated glutamic acid

<400> SEQUENCE: 7

Gly Asn Leu Xaa Arg
1               5

<210> SEQ ID NO 8
<211> LENGTH: 15
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as gamma-
      carboxylated glutamic acid
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid
<220> FEATURE:
<221> NAME/KEY: MISC_FEATURE
<222> LOCATION: (14)..(14)
<223> OTHER INFORMATION: Wherein X at position 14 is defined as gamma-
      carboxylated glutamic acid

<400> SEQUENCE: 8

Ala Asn Ala Phe Leu Xaa Xaa Leu Arg Pro Gly Ser Leu Xaa Arg
1               5                   10                  15

<210> SEQ ID NO 9
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: Wherein X at position 1 is defined as gamma-
      carboxylated glutamic acid
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid

<400> SEQUENCE: 9

Xaa Ile Phe Lys Asp Ala Xaa Arg
1               5

<210> SEQ ID NO 10
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein X at position 2 is defined as gamma-
      carboxylated glutamic acid
<220> FEATURE:
<221> NAME/KEY: MISC_FEATURE
<222> LOCATION: (3)..(3)
<223> OTHER INFORMATION: Wherein X at position 3 is defined as gamma-
      carboxylated glutamic acid
<220> FEATURE:
<221> NAME/KEY: MISC_FEATURE
<222> LOCATION: (10)..(10)
<223> OTHER INFORMATION: Wherein X at position 10 is defined as gamma-
      carboxylated glutamic acid

<400> SEQUENCE: 10

Leu Xaa Xaa Phe Val Gln Gly Asn Leu Xaa Arg
1               5                   10

<210> SEQ ID NO 11
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as gamma-
      carboxylated glutamic acid
<220> FEATURE:
<221> NAME/KEY: MISC_FEATURE
<222> LOCATION: (4)..(4)
<223> OTHER INFORMATION: Wherein X at position 4 is defined as gamma-
      carboxylated glutamic acid
<220> FEATURE:
<221> NAME/KEY: MISC_FEATURE
<222> LOCATION: (5)..(5)
<223> OTHER INFORMATION: Wherein X at position 5 is defined as gamma-
      carboxylated glutamic acid

<400> SEQUENCE: 11

Xaa Cys Met Xaa Xaa Lys
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
```

<222> LOCATION: (4)..(4)
<223> OTHER INFORMATION: Wherein X at position 4 is defined as gamma-
      carboxylated glutamic acid
<220> FEATURE:
<221> NAME/KEY: MISC_FEATURE
<222> LOCATION: (5)..(5)
<223> OTHER INFORMATION: Wherein X at position 5 is defined as gamma-
      carboxylated glutamic acid

<400> SEQUENCE: 12

Cys Ser Phe Xaa Xaa Ala Arg
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as gamma-
      carboxylated glutamic acid
<220> FEATURE:
<221> NAME/KEY: MISC_FEATURE
<222> LOCATION: (4)..(4)
<223> OTHER INFORMATION: Wherein X at position 4 is defined as gamma-
      carboxylated glutamic acid
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid

<400> SEQUENCE: 13

Xaa Val Phe Xaa Asn Thr Xaa Arg
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Wherein X at position 3 is defined as gamma-
      carboxylated glutamic acid

<400> SEQUENCE: 14

Thr Thr Xaa Phe Trp Lys
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as gamma-
      carboxylated glutamic acid
<220> FEATURE:
<221> NAME/KEY: MISC_FEATURE
<222> LOCATION: (4)..(4)
<223> OTHER INFORMATION: Wherein X at position 4 is defined as gamma-
      carboxylated glutamic acid

```
<400> SEQUENCE: 15

Xaa Val Phe Xaa Asp Ser Asp Lys
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Wherein X at position 3 is defined as gamma-
      carboxylated glutamic acid

<400> SEQUENCE: 16

Thr Asn Xaa Phe Trp Asn Lys
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as gamma-
      carboxylated glutamic acid
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid

<400> SEQUENCE: 17

Ala Asn Ser Leu Leu Xaa Xaa Thr Lys
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Wherein X at position 5 is defined as gamma-
      carboxylated glutamic acid

<400> SEQUENCE: 18

Gln Gly Asn Leu Xaa Arg
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as gamma-
      carboxylated glutamic acid
<220> FEATURE:
<221> NAME/KEY: MISC_FEATURE
```

```
<222> LOCATION: (4)..(4)
<223> OTHER INFORMATION: Wherein X at position 4 is defined as gamma-
      carboxylated glutamic acid
<220> FEATURE:
<221> NAME/KEY: MISC_FEATURE
<222> LOCATION: (5)..(5)
<223> OTHER INFORMATION: Wherein X at position 5 is defined as gamma-
      carboxylated glutamic acid

<400> SEQUENCE: 19

Xaa Cys Ile Xaa Xaa Leu Cys Asn Lys
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as gamma-
      carboxylated glutamic acid
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid

<400> SEQUENCE: 20

Ala Asn Ser Phe Leu Xaa Xaa Leu Arg
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Wherein X at position 5 is defined as gamma-
      carboxylated glutamic acid

<400> SEQUENCE: 21

His Ser Ser Leu Xaa Arg
1               5

<210> SEQ ID NO 22
<211> LENGTH: 15
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as gamma-
      carboxylated glutamic acid

<400> SEQUENCE: 22

Xaa Ile Phe Gln Asn Val Asp Asp Thr Leu Ala Phe Trp Ser Lys
1               5                   10                  15

<210> SEQ ID NO 23
<211> LENGTH: 19
<212> TYPE: PRT
<213> ORGANISM: Artificial sequence
<220> FEATURE:
```

```
<223> OTHER INFORMATION: Synthetic
<220> FEATURE:
<221> NAME/KEY: MISC_FEATURE
<222> LOCATION: (17)..(17)
<223> OTHER INFORMATION: Wherein X at position 17 is defined as gamma-
      carboxylated glutamic acid

<400> SEQUENCE: 23

Tyr Leu Tyr Gln Trp Leu Gly Ala Pro Val Pro Tyr Pro Asp Pro Leu
1               5                   10                  15

Xaa Pro Arg

<210> SEQ ID NO 24
<211> LENGTH: 23
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as gamma-
      carboxylated glutamic acid
<220> FEATURE:
<221> NAME/KEY: MISC_FEATURE
<222> LOCATION: (4)..(4)
<223> OTHER INFORMATION: Wherein X at position 4 is defined as gamma-
      carboxylated glutamic acid
<220> FEATURE:
<221> NAME/KEY: MISC_FEATURE
<222> LOCATION: (11)..(11)
<223> OTHER INFORMATION: Wherein X at position 11 is defined as gamma-
      carboxylated glutamic acid
<220> FEATURE:
<221> NAME/KEY: MISC_FEATURE
<222> LOCATION: (20)..(20)
<223> OTHER INFORMATION: Wherein X at position 20 is defined as gamma-
      carboxylated glutamic acid

<400> SEQUENCE: 24

Xaa Val Cys Xaa Leu Asn Pro Asp Cys Asp Xaa Leu Ala Asp His Ile
1               5                   10                  15

Gly Phe Gln Xaa Ala Tyr Arg
            20

<210> SEQ ID NO 25
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as gamma-
      carboxylated glutamic acid

<400> SEQUENCE: 25

Ser Lys Pro Val His Xaa Leu Asn Arg
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
```

<223> OTHER INFORMATION: Wherein X at position 1 is defined as gamma-
      carboxylated glutamic acid

<400> SEQUENCE: 26

Xaa Ala Cys Asp Asp Tyr Arg
1               5

<210> SEQ ID NO 27
<211> LENGTH: 15
<212> TYPE: PRT
<213> ORGANISM: Artificial sequence
<220> FEATURE:
<223> OTHER INFORMATION: Synthetic

<400> SEQUENCE: 27

Ala Asn Ala Phe Leu Glu Glu Leu Arg Pro Gly Ser Leu Glu Arg
1               5                   10                  15

<210> SEQ ID NO 28
<211> LENGTH: 8
<212> TYPE: PRT
<213> ORGANISM: Artificial sequence
<220> FEATURE:
<223> OTHER INFORMATION: Synthetic

<400> SEQUENCE: 28

Glu Ile Phe Lys Asp Ala Glu Arg
1               5

<210> SEQ ID NO 29
<211> LENGTH: 11
<212> TYPE: PRT
<213> ORGANISM: Artificial sequence
<220> FEATURE:
<223> OTHER INFORMATION: Synthetic

<400> SEQUENCE: 29

Leu Glu Glu Phe Val Gln Gly Asn Leu Glu Arg
1               5                   10

<210> SEQ ID NO 30
<211> LENGTH: 6
<212> TYPE: PRT
<213> ORGANISM: Artificial sequence
<220> FEATURE:
<223> OTHER INFORMATION: Synthetic

<400> SEQUENCE: 30

Glu Cys Met Glu Glu Lys
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic

<400> SEQUENCE: 31

Cys Ser Phe Glu Glu Ala Arg
1               5

<210> SEQ ID NO 32
<211> LENGTH: 8
<212> TYPE: PRT
<213> ORGANISM: Artificial sequence
<220> FEATURE:

```
<223> OTHER INFORMATION: Synthetic

<400> SEQUENCE: 32

Glu Val Phe Glu Asn Thr Glu Arg
1               5

<210> SEQ ID NO 33
<211> LENGTH: 6
<212> TYPE: PRT
<213> ORGANISM: Artificial sequence
<220> FEATURE:
<223> OTHER INFORMATION: Synthetic

<400> SEQUENCE: 33

Thr Thr Glu Phe Trp Lys
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic

<400> SEQUENCE: 34

Ala Asn Ser Phe Leu Glu Glu Met Lys
1               5

<210> SEQ ID NO 35
<211> LENGTH: 8
<212> TYPE: PRT
<213> ORGANISM: Artificial sequence
<220> FEATURE:
<223> OTHER INFORMATION: Synthetic

<400> SEQUENCE: 35

Glu Val Phe Glu Asp Ser Asp Lys
1               5

<210> SEQ ID NO 36
<211> LENGTH: 7
<212> TYPE: PRT
<213> ORGANISM: Artificial sequence
<220> FEATURE:
<223> OTHER INFORMATION: Synthetic

<400> SEQUENCE: 36

Thr Asn Glu Phe Trp Asn Lys
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic

<400> SEQUENCE: 37

Ala Asn Ser Leu Leu Glu Glu Thr Lys
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic
```

```
<400> SEQUENCE: 38

Gln Gly Asn Leu Glu Arg
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic

<400> SEQUENCE: 39

Glu Cys Ile Glu Glu Leu Cys Asn Lys
1               5

<210> SEQ ID NO 40
<211> LENGTH: 9
<212> TYPE: PRT
<213> ORGANISM: Artificial sequence
<220> FEATURE:
<223> OTHER INFORMATION: Synthetic

<400> SEQUENCE: 40

Ala Asn Ser Phe Leu Glu Glu Leu Arg
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic

<400> SEQUENCE: 41

His Ser Ser Leu Glu Arg
1               5

<210> SEQ ID NO 42
<211> LENGTH: 15
<212> TYPE: PRT
<213> ORGANISM: Artificial sequence
<220> FEATURE:
<223> OTHER INFORMATION: Synthetic

<400> SEQUENCE: 42

Glu Ile Phe Gln Asn Val Asp Asp Thr Leu Ala Phe Trp Ser Lys
1               5                   10                  15

<210> SEQ ID NO 43
<211> LENGTH: 19
<212> TYPE: PRT
<213> ORGANISM: Artificial sequence
<220> FEATURE:
<223> OTHER INFORMATION: Synthetic

<400> SEQUENCE: 43

Tyr Leu Tyr Gln Trp Leu Gly Ala Pro Val Pro Tyr Pro Asp Pro Leu
1               5                   10                  15

Glu Pro Arg

<210> SEQ ID NO 44
<211> LENGTH: 23
<212> TYPE: PRT
<213> ORGANISM: Artificial sequence
<220> FEATURE:
```

<223> OTHER INFORMATION: Synthetic

<400> SEQUENCE: 44

Glu Val Cys Glu Leu Asn Pro Asp Cys Asp Glu Leu Ala Asp His Ile
1               5                   10                  15
Gly Phe Gln Glu Ala Tyr Arg
            20

<210> SEQ ID NO 45
<211> LENGTH: 9
<212> TYPE: PRT
<213> ORGANISM: Artificial sequence
<220> FEATURE:
<223> OTHER INFORMATION: Synthetic

<400> SEQUENCE: 45

Ser Lys Pro Val His Glu Leu Asn Arg
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic

<400> SEQUENCE: 46

Glu Ala Cys Asp Asp Tyr Arg
1               5

<210> SEQ ID NO 47
<211> LENGTH: 9
<212> TYPE: PRT
<213> ORGANISM: Artificial sequence
<220> FEATURE:
<223> OTHER INFORMATION: Synthetic

<400> SEQUENCE: 47

Ser Gly Ile Glu Cys Gln Leu Trp Arg
1               5

<210> SEQ ID NO 48
<211> LENGTH: 13
<212> TYPE: PRT
<213> ORGANISM: Artificial sequence
<220> FEATURE:
<223> OTHER INFORMATION: Synthetic

<400> SEQUENCE: 48

Thr Ala Thr Ser Glu Tyr Gln Thr Phe Phe Asn Pro Arg
1               5                   10

<210> SEQ ID NO 49
<211> LENGTH: 10
<212> TYPE: PRT
<213> ORGANISM: Artificial sequence
<220> FEATURE:
<223> OTHER INFORMATION: Synthetic

<400> SEQUENCE: 49

Glu Leu Leu Glu Ser Tyr Ile Asp Gly Arg
1               5                   10

<210> SEQ ID NO 50
<211> LENGTH: 9
<212> TYPE: PRT

```
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as gamma-
      carboxylated glutamic acid
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid

<400> SEQUENCE: 50

Ala Asn Ala Phe Leu Xaa Xaa Leu Arg
1               5

<210> SEQ ID NO 51
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Wherein X at position 5 is defined as gamma-
      carboxylated glutamic acid

<400> SEQUENCE: 51

Pro Gly Ser Leu Xaa Arg
1               5

<210> SEQ ID NO 52
<211> LENGTH: 9
<212> TYPE: PRT
<213> ORGANISM: Artificial sequence
<220> FEATURE:
<223> OTHER INFORMATION: Synthetic

<400> SEQUENCE: 52

Ala Asn Ala Phe Leu Glu Glu Leu Arg
1               5

<210> SEQ ID NO 53
<211> LENGTH: 6
<212> TYPE: PRT
<213> ORGANISM: Artificial sequence
<220> FEATURE:
<223> OTHER INFORMATION: Synthetic

<400> SEQUENCE: 53

Pro Gly Ser Leu Glu Arg
1               5

<210> SEQ ID NO 54
<211> LENGTH: 10
<212> TYPE: PRT
<213> ORGANISM: Artificial sequence
<220> FEATURE:
<223> OTHER INFORMATION: Synthetic

<400> SEQUENCE: 54

Ser Glu Pro Arg Pro Gly Val Leu Leu Arg
1               5                   10

<210> SEQ ID NO 55
<211> LENGTH: 10
```

```
<212> TYPE: PRT
<213> ORGANISM: Artificial sequence
<220> FEATURE:
<223> OTHER INFORMATION: Synthetic

<400> SEQUENCE: 55

Val Ser Gln Tyr Ile Glu Trp Leu Gln Lys
1               5                   10

<210> SEQ ID NO 56
<211> LENGTH: 6
<212> TYPE: PRT
<213> ORGANISM: Artificial sequence
<220> FEATURE:
<223> OTHER INFORMATION: Synthetic

<400> SEQUENCE: 56

Thr Leu Ala Phe Val Arg
1               5

<210> SEQ ID NO 57
<211> LENGTH: 11
<212> TYPE: PRT
<213> ORGANISM: Artificial sequence
<220> FEATURE:
<223> OTHER INFORMATION: Synthetic

<400> SEQUENCE: 57

Phe Gly Ser Gly Tyr Val Ser Gly Trp Gly Arg
1               5                   10

<210> SEQ ID NO 58
<211> LENGTH: 9
<212> TYPE: PRT
<213> ORGANISM: Artificial sequence
<220> FEATURE:
<223> OTHER INFORMATION: Synthetic

<400> SEQUENCE: 58

Ser Ala Leu Val Leu Gln Tyr Leu Arg
1               5

<210> SEQ ID NO 59
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Wherein X at position 4 is defined as gamma-
      carboxylated glutamic acid

<400> SEQUENCE: 59

Gly His Leu Xaa Arg
1               5

<210> SEQ ID NO 60
<211> LENGTH: 5
<212> TYPE: PRT
<213> ORGANISM: Artificial sequence
<220> FEATURE:
<223> OTHER INFORMATION: Synthetic

<400> SEQUENCE: 60

Gly His Leu Glu Arg
1               5
```

```
<210> SEQ ID NO 61
<211> LENGTH: 9
<212> TYPE: PRT
<213> ORGANISM: Artificial sequence
<220> FEATURE:
<223> OTHER INFORMATION: Synthetic

<400> SEQUENCE: 61

Thr Gly Ile Val Ser Gly Phe Gly Arg
1               5

<210> SEQ ID NO 62
<211> LENGTH: 9
<212> TYPE: PRT
<213> ORGANISM: Artificial sequence
<220> FEATURE:
<223> OTHER INFORMATION: Synthetic

<400> SEQUENCE: 62

Met Leu Glu Val Pro Tyr Val Asp Arg
1               5

<210> SEQ ID NO 63
<211> LENGTH: 12
<212> TYPE: PRT
<213> ORGANISM: Artificial sequence
<220> FEATURE:
<223> OTHER INFORMATION: Synthetic

<400> SEQUENCE: 63

Asp Thr Glu Asp Gln Glu Asp Gln Val Asp Pro Arg
1               5                   10

<210> SEQ ID NO 64
<211> LENGTH: 8
<212> TYPE: PRT
<213> ORGANISM: Artificial sequence
<220> FEATURE:
<223> OTHER INFORMATION: Synthetic

<400> SEQUENCE: 64

Thr Phe Val Leu Asn Phe Ile Lys
1               5

<210> SEQ ID NO 65
<211> LENGTH: 6
<212> TYPE: PRT
<213> ORGANISM: Artificial sequence
<220> FEATURE:
<223> OTHER INFORMATION: Synthetic

<400> SEQUENCE: 65

Tyr Leu Val Cys Leu Arg
1               5

<210> SEQ ID NO 66
<211> LENGTH: 8
<212> TYPE: PRT
<213> ORGANISM: Artificial sequence
<220> FEATURE:
<223> OTHER INFORMATION: Synthetic

<400> SEQUENCE: 66

Val Tyr Phe Ala Gly Phe Pro Arg
1               5
```

```
<210> SEQ ID NO 67
<211> LENGTH: 7
<212> TYPE: PRT
<213> ORGANISM: Artificial sequence
<220> FEATURE:
<223> OTHER INFORMATION: Synthetic

<400> SEQUENCE: 67

Gln Leu Ala Val Leu Asp Lys
1               5

<210> SEQ ID NO 68
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Wherein X at position 7 is defined as gamma-
      carboxylated glutamic acid
<220> FEATURE:
<221> NAME/KEY: MISC_FEATURE
<222> LOCATION: (8)..(8)
<223> OTHER INFORMATION: Wherein X at position 8 is defined as gamma-
      carboxylated glutamic acid
<220> FEATURE:
<221> NAME/KEY: MISC_FEATURE
<222> LOCATION: (11)..(11)
<223> OTHER INFORMATION: Wherein X at position 11 is defined as gamma-
      carboxylated glutamic acid
<220> FEATURE:
<221> NAME/KEY: MISC_FEATURE
<222> LOCATION: (15)..(15)
<223> OTHER INFORMATION: Wherein X at position 15 is defined as gamma-
      carboxylated glutamic acid

<400> SEQUENCE: 68

Ala Gly Ser Tyr Leu Leu Xaa Xaa Leu Phe Xaa Gly Asn Leu Xaa Lys
1               5                   10                  15

<210> SEQ ID NO 69
<211> LENGTH: 16
<212> TYPE: PRT
<213> ORGANISM: Artificial sequence
<220> FEATURE:
<223> OTHER INFORMATION: Synthetic

<400> SEQUENCE: 69

Ala Gly Ser Tyr Leu Leu Glu Glu Leu Phe Glu Gly Asn Leu Glu Lys
1               5                   10                  15

<210> SEQ ID NO 70
<211> LENGTH: 9
<212> TYPE: PRT
<213> ORGANISM: Artificial sequence
<220> FEATURE:
<223> OTHER INFORMATION: Synthetic

<400> SEQUENCE: 70

Glu Asn Phe Val Leu Thr Thr Ala Lys
1               5

<210> SEQ ID NO 71
<211> LENGTH: 8
<212> TYPE: PRT
<213> ORGANISM: Artificial sequence
<220> FEATURE:
<223> OTHER INFORMATION: Synthetic
```

```
<400> SEQUENCE: 71

Gly Leu Leu Ser Gly Trp Ala Arg
1               5

<210> SEQ ID NO 72
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as E-(CH3)2
      (derivatized gamma-carboxylated glutamic acid)
<220> FEATURE:
<221> NAME/KEY: MISC_FEATURE
<222> LOCATION: (7)..(7)
<223> OTHER INFORMATION: Wherein X at position 7 is defined as E-(CH3)2
      (derivatized gamma-carboxylated glutamic acid)
<220> FEATURE:
<221> NAME/KEY: MISC_FEATURE
<222> LOCATION: (9)..(9)
<223> OTHER INFORMATION: Wherein X at position 9 is defined as R-CH3
      (derivatized carboxyl terminal arginine)

<400> SEQUENCE: 72

Ala Asn Thr Phe Leu Xaa Xaa Val Xaa
1               5

<210> SEQ ID NO 73
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein X at position 6 is defined as E-(CH3)2
      (derivatized gamma-carboxylated glutamic acid)
<220> FEATURE:
<221> NAME/KEY: MISC_FEATURE
<222> LOCATION: (7)..(7)
<223> OTHER INFORMATION: Wherein X at position 7 is defined as E-(CH3)2
      (derivatized gamma-carboxylated glutamic acid)
<220> FEATURE:
<221> NAME/KEY: MISC_FEATURE
<222> LOCATION: (10)..(10)
<223> OTHER INFORMATION: Wherein X at position 10 is defined as K-CH3
      (derivatized carboxyl terminal lysine)

<400> SEQUENCE: 73

Ala Asn Thr Phe Leu Xaa Xaa Val Arg Xaa
1               5                   10

<210> SEQ ID NO 74
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Wherein X at position 5 is defined as
      C-carbamidomethyl (Cysteine with carbamidomethyl bound to the
      cysteine sulfur atom)
```

```
<400> SEQUENCE: 74

Ser Gly Ile Glu Xaa Gln Leu Trp Arg
1               5

<210> SEQ ID NO 75
<211> LENGTH: 17
<212> TYPE: PRT
<213> ORGANISM: Artificial sequence
<220> FEATURE:
<223> OTHER INFORMATION: Synthetic

<400> SEQUENCE: 75

Val Phe Asp Glu Phe Lys Pro Leu Val Glu Glu Pro Gln Asn Leu Ile
1               5                   10                  15

Lys

<210> SEQ ID NO 76
<211> LENGTH: 10
<212> TYPE: PRT
<213> ORGANISM: Artificial sequence
<220> FEATURE:
<223> OTHER INFORMATION: Synthetic

<400> SEQUENCE: 76

Leu Val Asn Glu Val Thr Glu Phe Ala Lys
1               5                   10

<210> SEQ ID NO 77
<211> LENGTH: 10
<212> TYPE: PRT
<213> ORGANISM: Artificial sequence
<220> FEATURE:
<223> OTHER INFORMATION: Synthetic

<400> SEQUENCE: 77

Glu Leu Leu Glu Ser Thr Ile Asp Gly Arg
1               5                   10
```

QUANTITATION OF GLA PROTEINS BY MASS SPECTROMETRIC ANALYSIS

CROSS-REFERENCE TO RELATED APPLICATION

This application claims the benefit of U.S. Application No. 63/057,730, filed Jul. 28, 2020, expressly incorporated herein by reference in its entirety.

STATEMENT OF GOVERNMENT LICENSE RIGHTS

This invention was made with government support under Grant No. P01 GM116691, awarded by the National Institutes of Health. The government has certain rights in the invention.

BACKGROUND OF THE INVENTION

Active prothrombin (Factor II) comprises ten γ-carboxylated glutamic acid (Gla) residues, which are formed post-translationally by vitamin K-dependent hepatic γ-glutamyl carboxylase (GGCX) during prothrombin biosynthesis in the liver. Certain anti-coagulants, such as warfarin, exhibit their anticoagulant effect by inhibiting the recycling of vitamin K epoxide to the reduced form of vitamin K. Reduced vitamin K is a cofactor used by GGCX, and its inhibition thereby decreases the synthesis of active prothrombin. Significant inter-individual variability in the warfarin pharmacodynamic response exists, which can be partly explained by demographic and clinical factors, as well as genetic polymorphisms in the following: i) warfarin metabolizing enzyme, i.e., cytochrome P450 2C9 (CYP2C9); ii) warfarin target receptor, vitamin K epoxide reductase complex subunit 1 (VKORC1); and iii) vitamin K catabolizing enzyme, CYP4F2. Inter- and intra-individual variability in warfarin response can also arise due to drug interactions affecting warfarin metabolism, liver dysfunction, and alteration in dietary vitamin K intake.

International normalized ratio (INR) is a functional assay of pharmacodynamic response to anticoagulation therapy that measures part of the blood clotting process (prothrombin time) affected by warfarin and similar anticoagulants during a pre-specified time of measurement, normalized for laboratory variation. INR is used as a biomarker of warfarin efficacy to avoid adverse events associated with both under- and over-anticoagulation. Adverse events associated with under-anticoagulation include thrombus formation in at-risk patients, leading to stroke, cardiovascular events, or pulmonary embolism. Adverse events associated with over-anticoagulation include bruising, prolonged bleeding, and in the most severe state, hemorrhagic stroke or life-threatening bleeding in other tissues of the body such as the gastrointestinal tract. An INR value greater than 4 is associated with an increased risk of bleeding, with the risk of intracranial hemorrhage increasing approximately 2-fold for every one-unit rise in INR above 4.

INR assay readouts can be affected by methodological variables, such as the blood collection procedure and sample handling temperature and duration. Moreover, depending on the half-life of vitamin K-dependent coagulation factors, a time-lag exists between a warfarin dose and initiation of the therapeutic response. For example, during the initial days of warfarin therapy, prolongation of INR correlates with a decline in factor VII (half-life 4-6 hr), whereas the effect of altered prothrombin on INR appears later (half-life 60-70 hr).

To address the mechanistic limitations of INR, quantitation of under-γ-carboxylated forms of prothrombin in plasma, also referred to as protein induced by vitamin K antagonist-II (PIVKA-II), has been adopted and is considered a more specific and long-term marker of prothrombin activity. Vitamin K deficiency, warfarin treatment, and liver dysfunction (e.g., hepatic carcinoma) all lead to PIVKA-II build-up in the blood. PIVKA-II in plasma exists as a mixture of proteoforms with a variable number (1-9) of non-carboxylated glutamate residues in the prothrombin Gla domain in warfarin-treated patients.

Although an enzyme-linked immunosorbent assay (ELISA) method exists for plasma PIVKA-II quantification, the ELISA method is incapable of distinguishing between the different γ-carboxylated proteoforms. The different γ-carboxylation states are proteoforms with varying numbers of γ-carboxylated glutamate or glutamic acid residues in the Gla domain, some of which have activity. For example, the activity of prothrombin is defined by its carboxylation states, where the presence of eight (8) or nine (9) post-translational γ-carboxylation events (GC-8 and GC-9) results in at least partial prothrombin activity, and the presence of ten (10) post-translational γ-carboxylation events maintains complete activity. The absence of three (3) or more carboxylation modifications results in nearly complete loss of activity. The ELISA assay does not allow simultaneous quantification of total, active (fully γ-carboxylated), partially-active (proteoforms having at least one, but fewer than all, glutamate or glutamic acid residues being γ-carboxylated), and inactive (des-carboxylated) prothrombin. Additionally, to our knowledge, no validated ELISA method currently exists for detecting Factor VII, Factor IX, Factor X, the anticoagulant proteins C and S, the factor X-targeting protein Z, the growth arrest specific gene 6 protein (GAS6), periostin, transmembrane Gla proteins (TMGPs), transthyretin (thyroxin binding protein), and proline-rich Gla-proteins (PRGPs).

A need therefore exists for sensitive and accurate methods to quantify proteins capable of post-translational modification, specifically γ-carboxylation and the resultant fully γ-carboxylated, partially γ-carboxylated, and des-carboxylated proteins derived from vitamin K-dependent blood clotting factors such as prothrombin.

SUMMARY OF THE INVENTION

The object of the present invention is to solve the aforementioned problems with current methods for detecting γ-carboxylated proteins through providing a novel method for detecting γ-carboxylated proteins derived from vitamin K-dependent blood clotting factors such as prothrombin.

A significant advantage of the present invention method is its requirement of only a 10 biological sample such as blood, plasma, or a dried blood spot. In the present invention, the proteins in the biological sample derived from a blood clotting factor are first concentrated by extraction, subject to proteolytic cleavage, and the resultant γ-carboxylated peptides, γ-carboxylated peptide proteoforms, and des-carboxylated peptides collected and analyzed.

The present invention method provides rapid detection of fully γ-carboxylated peptides, γ-carboxylated peptide proteoforms, and des-carboxylated peptides, through LC-MS or LC-MS/MS detection. The method additionally utilizes reaction monitoring of a fragmentation profile for each peptide detected. Increased mass spectrometry signal response and peptide detection is achieved through derivatization of the Gla amino acid side chain carboxyl moiety of the γ-carboxylated peptides, γ-carboxylated peptide proteoforms, and des-carboxylated peptides.

The resultant determination of the quantity of such peptides provides a profile of the Gla-region peptides. Such a profile can be used in the administration of anticoagulant therapies for a subject in need, such as for determining the dose of an anticoagulant therapy such as warfarin. Additionally, when the resultant profile is compared to a control sample, it provides a method of diagnosing blood clotting-related conditions in a subject, such as hepatocellular carcinoma, Sars-CoV-2 (COVID-19), and cancer.

In one aspect, the invention provides a method for quantifying one or more of γ-carboxylated proteins, γ-carboxylated protein proteoforms, and des-carboxylated proteins in a biological sample. In certain embodiments, the method comprises:

(a) extracting a sample comprising one or more of γ-carboxylated proteins, γ-carboxylated protein proteoforms, and des-carboxylated proteins from the biological sample having a first concentration, to provide a solution having a second concentration comprising one or more of γ-carboxylated proteins, γ-carboxylated protein proteoforms, and des-carboxylated proteins;

(b) contacting the γ-carboxylated proteins, γ-carboxylated protein proteoforms, and des-carboxylated proteins in the solution having the second concentration with a protease, to provide a solution of peptides comprising one or more of γ-carboxylated peptides, γ-carboxylated peptide proteoforms, and des-carboxylated peptides; and (c) determining the quantity of the one or more of γ-carboxylated peptides, γ-carboxylated peptide proteoforms, and des-carboxylated peptides in the solution of peptides.

In another aspect, the invention provides a method for quantifying one or more of γ-carboxylated proteins, γ-carboxylated protein proteoforms, and des-carboxylated proteins in a biological sample using a peptide derivatization step. In certain embodiments, the method comprises:

(a) extracting a sample comprising one or more of γ-carboxylated proteins, γ-carboxylated protein proteoforms, and des-carboxylated proteins from the biological sample having a first concentration, to provide a solution having a second concentration comprising one or more of γ-carboxylated proteins, γ-carboxylated protein proteoforms, and des-carboxylated proteins;

(b) contacting the γ-carboxylated proteins, γ-carboxylated protein proteoforms, and des-carboxylated proteins in the solution having the second concentration with a protease, to provide a solution of peptides comprising one or more of γ-carboxylated peptides, γ-carboxylated peptide proteoforms, and des-carboxylated peptides;

(c) derivatizing the one or more of γ-carboxylated peptides, γ-carboxylated peptide proteoforms, and des-carboxylated peptides of the solution of peptides, to provide one or more derivatized γ-carboxylated peptides, derivatized γ-carboxylated peptide proteoforms, and derivatized des-carboxylated peptides; and (d) determining the quantity of the one or more of derivatized γ-carboxylated peptides, derivatized γ-carboxylated peptide proteoforms, and derivatized des-carboxylated peptides in the solution of peptides.

In the above methods, representative γ-carboxylated proteins, γ-carboxylated protein proteoforms, and des-carboxylated proteins are derived from one or more vitamin K-dependent blood clotting factors.

In embodiments of the above methods, the quantity of the one or more of γ-carboxylated peptides, γ-carboxylated peptide proteoforms, and des-carboxylated peptides is determined by mass spectrometric (MS) analysis.

In other aspects of the invention, the above methods for quantifying one or more of γ-carboxylated proteins, γ-carboxylated protein proteoforms, and des-carboxylated proteins are used in a method for administering an anticoagulant to a subject in need thereof. In certain embodiments, the method comprises:

(a) determining the quantity of one or more of γ-carboxylated peptides, γ-carboxylated peptide proteoforms, and des-carboxylated peptides according to one of above methods as described herein;

(b) determining a therapeutically effective dose of an anticoagulant to be administered based on the quantity of one or more of γ-carboxylated peptides, γ-carboxylated peptide proteoforms, and des-carboxylated peptides; and (c) administering the therapeutically effective dose of the anticoagulant to the subject.

In certain embodiments, the anticoagulant is a vitamin K pathway inhibitor. Representative anticoagulants include warfarin, dabigatran, rivaroxaban, apixaban, betrixaban, and edoxaban.

In further aspects of the invention, the above methods for quantifying one or more of γ-carboxylated proteins, γ-carboxylated protein proteoforms, and des-carboxylated proteins are used in a method for diagnosing hepatocellular carcinoma (HCC) in a subject. In certain embodiments, the method comprises:

(a) determining the quantity of one or more of γ-carboxylated peptides, γ-carboxylated peptide proteoforms, and des-carboxylated peptides according to one of above methods as described herein;

(b) comparing the quantity of one or more of γ-carboxylated peptides, γ-carboxylated peptide proteoforms, and des-carboxylated peptides with a quantity of one or more of γ-carboxylated peptides, γ-carboxylated peptide proteoforms, and des-carboxylated peptides obtained from a control sample; and (c) diagnosing HCC in the subject based on comparing the amounts of one or more of γ-carboxylated peptides, γ-carboxylated peptide proteoforms, and des-carboxylated peptides from the subject and the control sample, wherein a difference between the quantified amounts greater than a predetermined threshold is diagnostic of HCC.

In certain embodiments, the γ-carboxylated peptides, γ-carboxylated peptide proteoforms, or des-carboxylated peptides are derived from prothrombin (Factor II).

DESCRIPTION OF THE DRAWINGS

The foregoing aspects and many of the attendant advantages of this invention will become more readily appreciated as the same become better understood by reference to the following detailed description, when taken in conjunction with the accompanying drawings.

(CH₃)₂][E-(CH₃)₂]MK-CH₃ (SEQ ID NO: 2), confirming methylation and increased signal response for the derivatized peptide.

Figure 4:
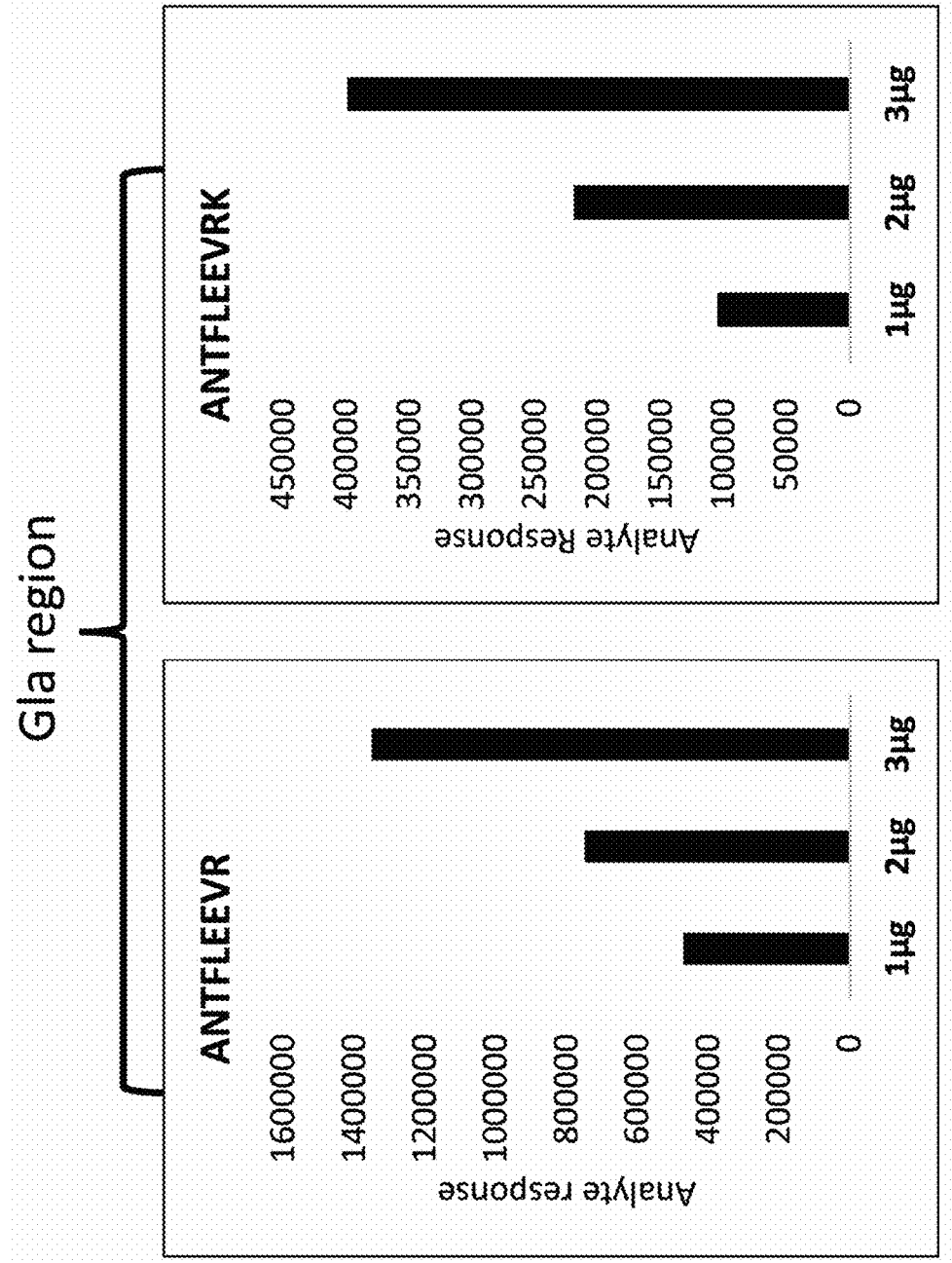

FIG. 4 shows Gla region methyl ester mass spectrometry signal increase with increasing amounts of Gla-region peptides for Factor II.

Figure 5A:
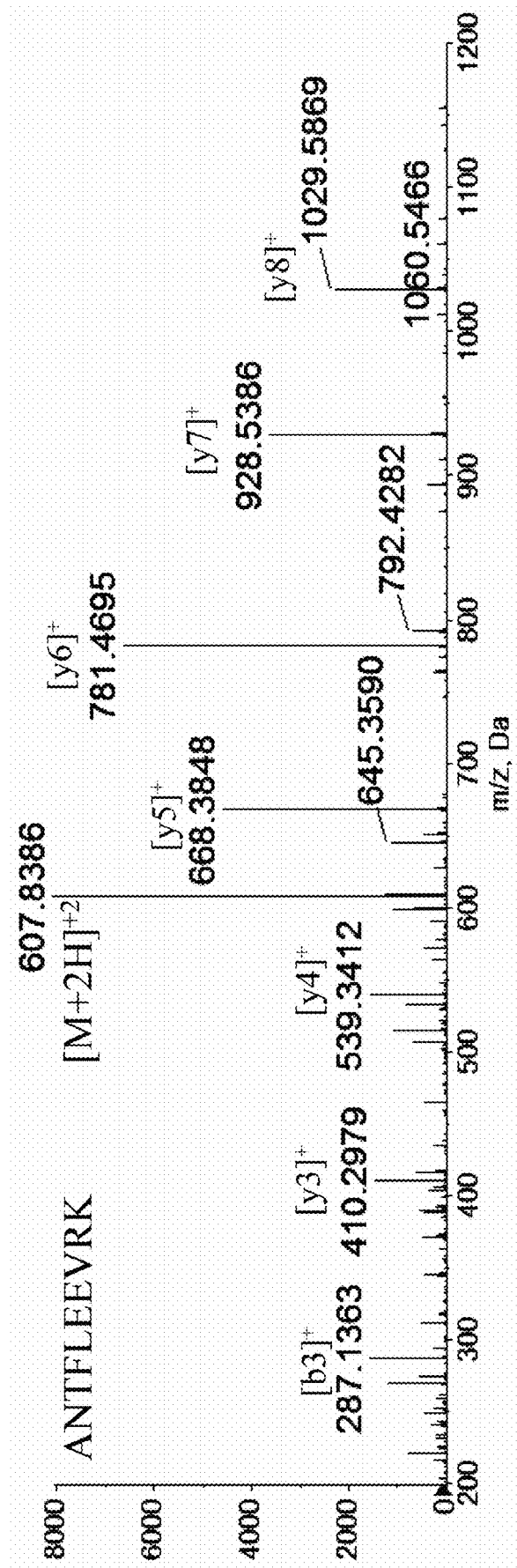
Figure 5B:
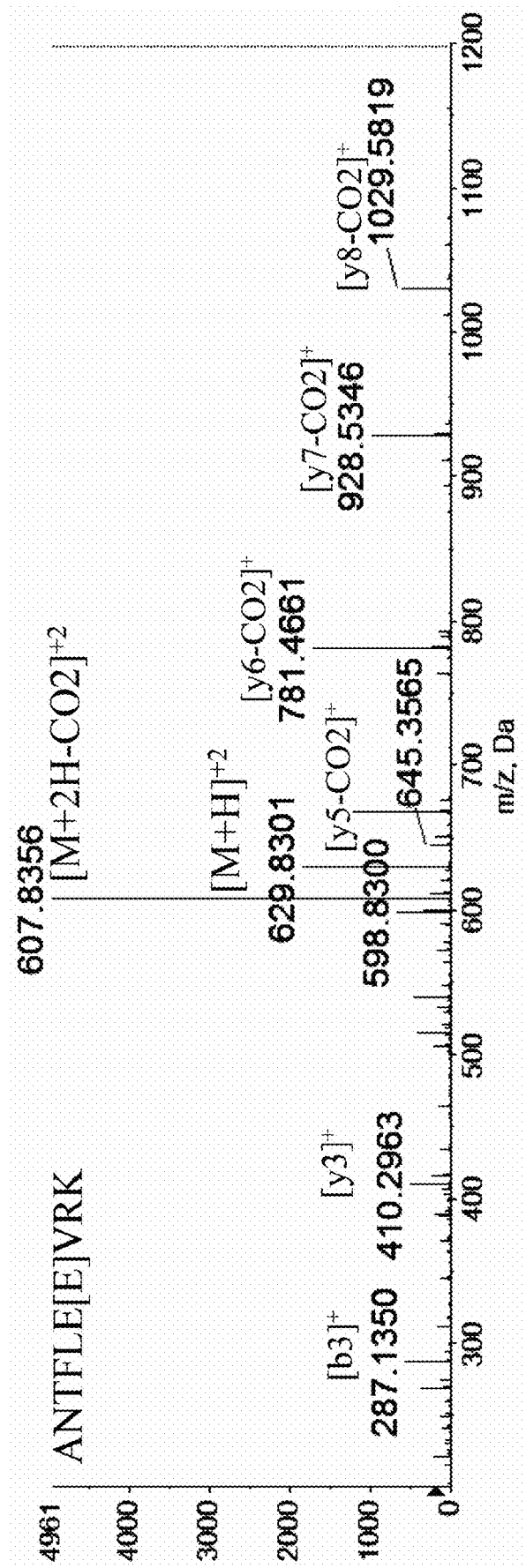
Figure 5C:
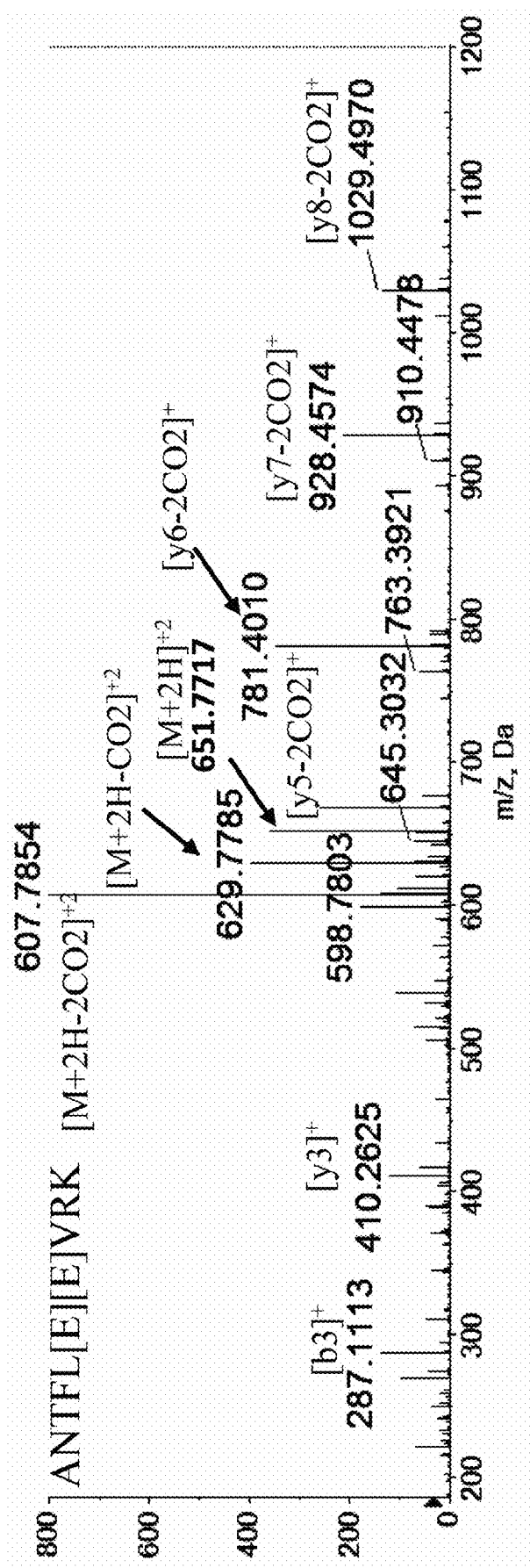

FIG. 5A shows the MS/MS spectrum of des-carboxy peptide ANTFLEEVRK (SEQ ID NO: 3), showing the parent ion and dominant fragment γ-ions. FIG. 5B shows the MS/MS spectrum of mono-carboxy peptide ANTFLE[E]VRK (SEQ ID NO: 4), showing the parent ion and dominant fragments comprising $CO_2$ loss (γ-$CO_2$). FIG. 5C shows the MS/MS spectrum of the di-carboxy peptide ANTFL[E][E]VRK (SEQ ID NO: 5), showing the parent ion and dominant fragments comprising loss of two $CO_2$ moieties (γ-2$CO_2$).

Figure 6A:
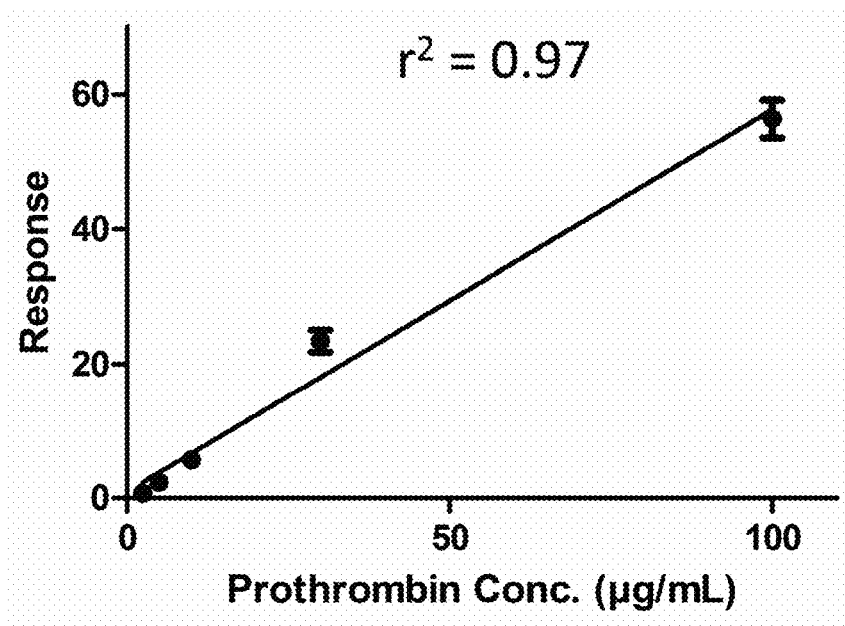
Figure 6B:
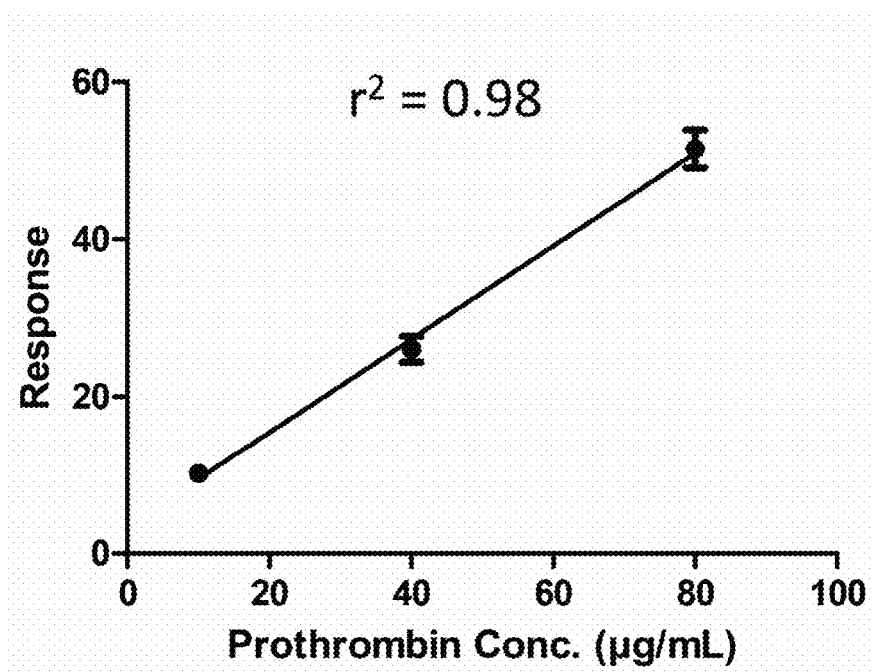
Figure 6C:
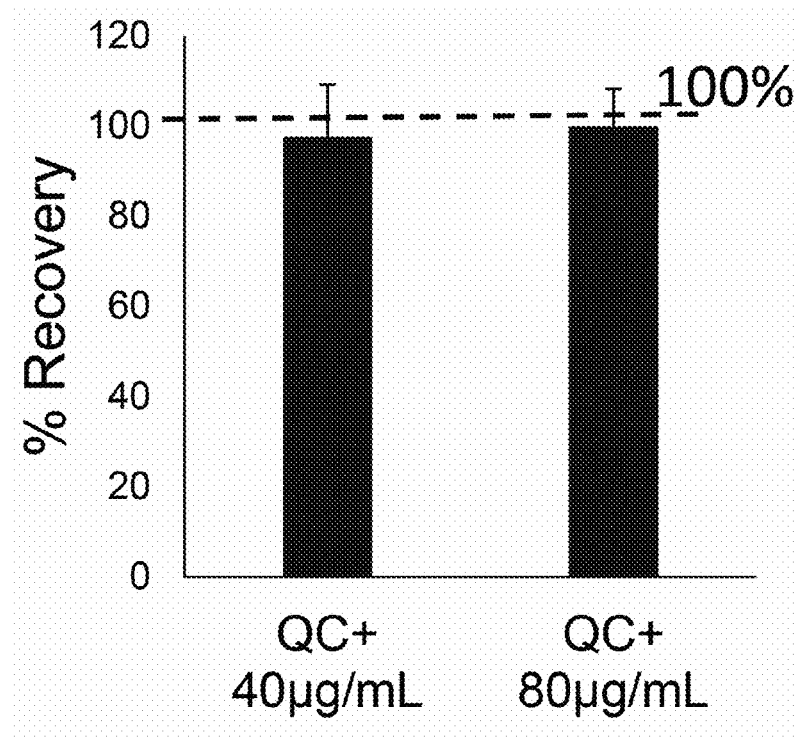

FIGS. 6A and 6B are LC-MS/MS assay performance diagrams wherein the linearity was determined by spiking heavy peptide into human serum albumin and human serum matrix. FIG. 6C shows the percent recovery calculated by spiking the standard prothrombin into pooled control serum samples.

Figure 7A:
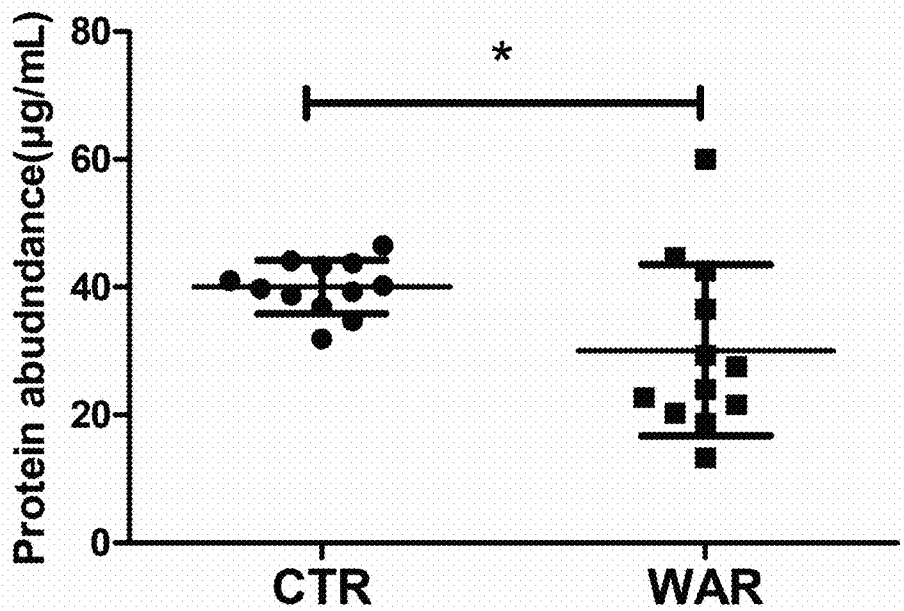
Figure 7B:
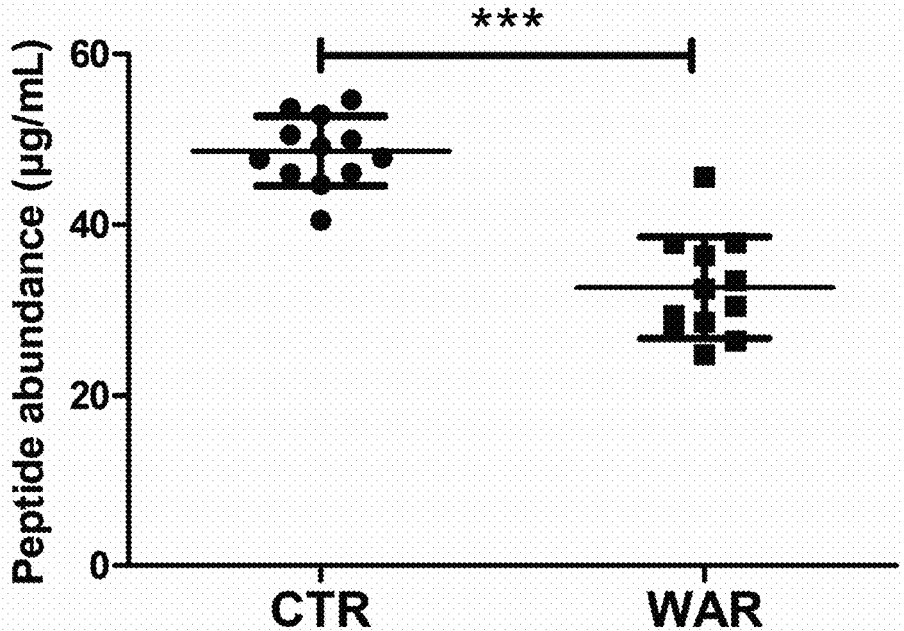
Figure 7C:
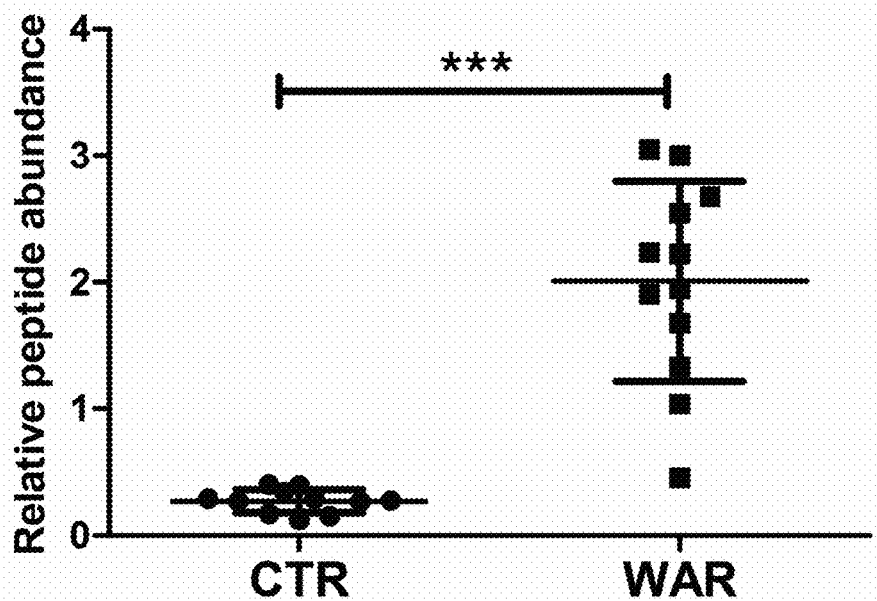
Figure 7D:
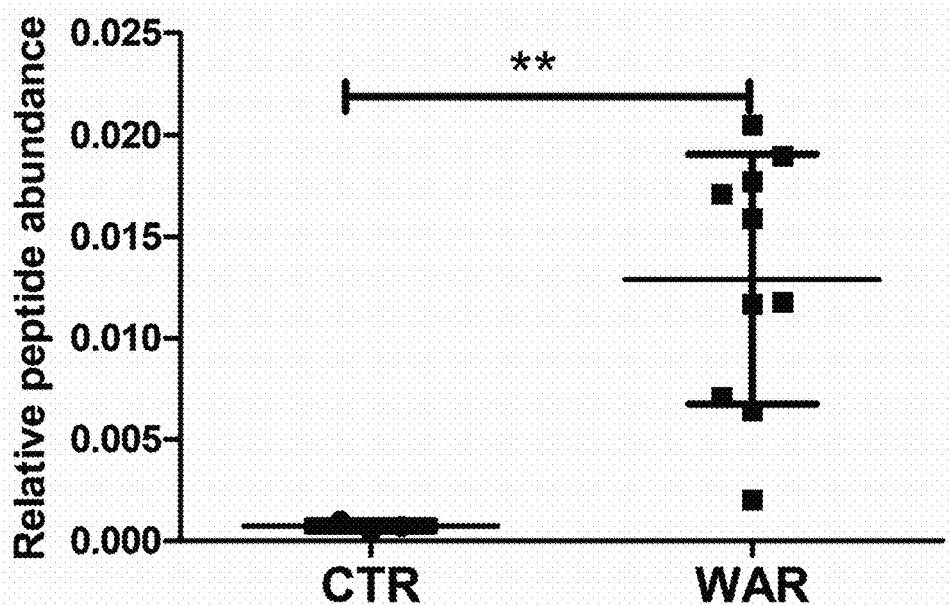

FIG. 7A shows a comparison of total prothrombin abundance in serum samples from control and warfarin-treated individuals. FIG. 7B shows a comparison of γ-carboxy peptide ANTFL[E][E]VRK (SEQ ID NO: 5) in serum samples from control and warfarin-treated individuals. FIGS. 7C and 7D show des-carboxy peptides GNLER (SEQ ID NO: 6) and ANTFLEEVRK (SEQ ID NO: 3) respectively in serum samples from control and warfarin-treated individuals.

Figures 8A, 8B:
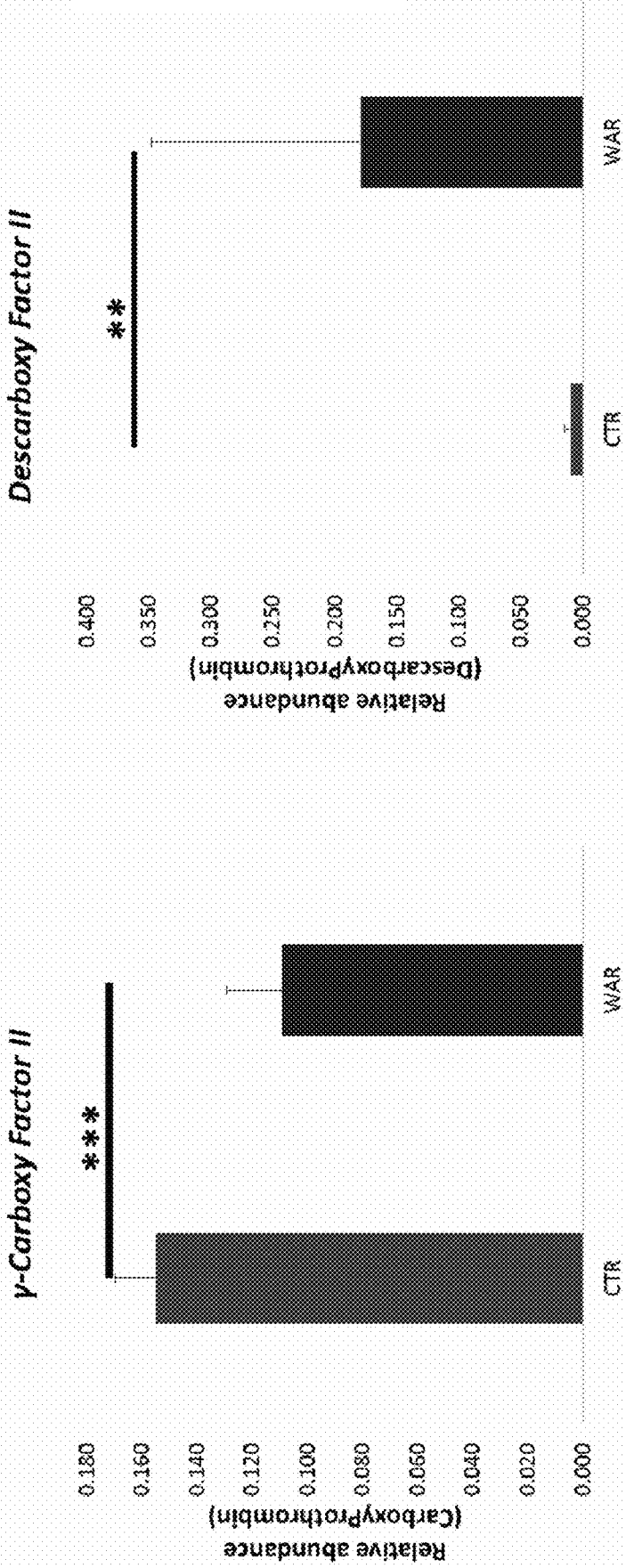

FIG. 8A shows the relative abundance of γ-carboxy prothrombin in control samples and warfarin-treated samples. FIG. 8B shows the relative abundance of des-carboxy prothrombin in control samples and warfarin-treated samples.

Figure 9A:
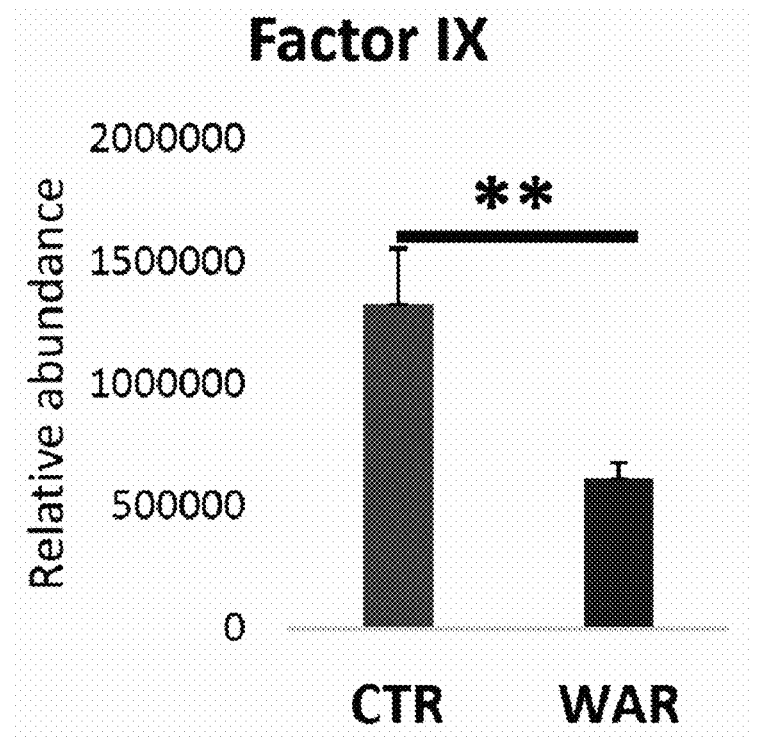
Figure 9B:
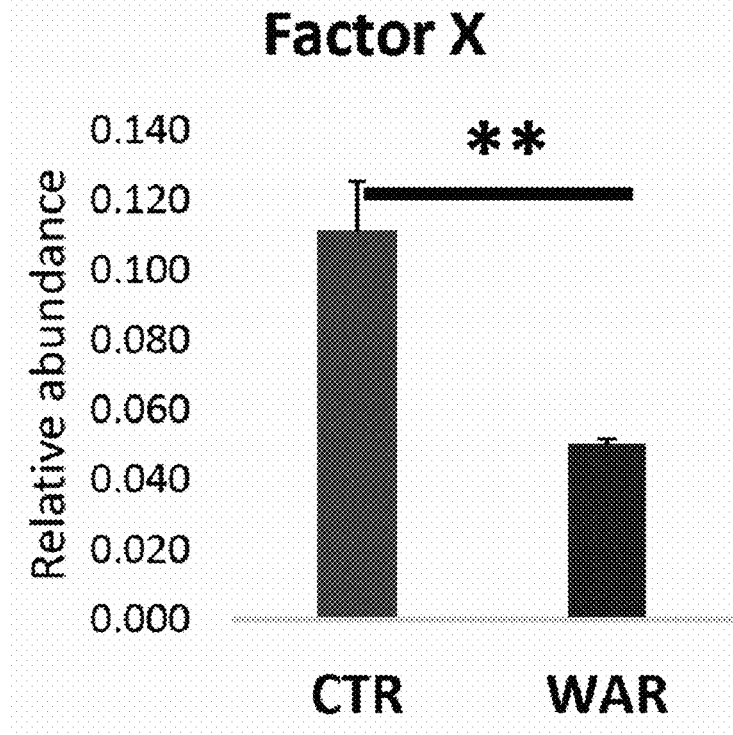
Figure 9C:
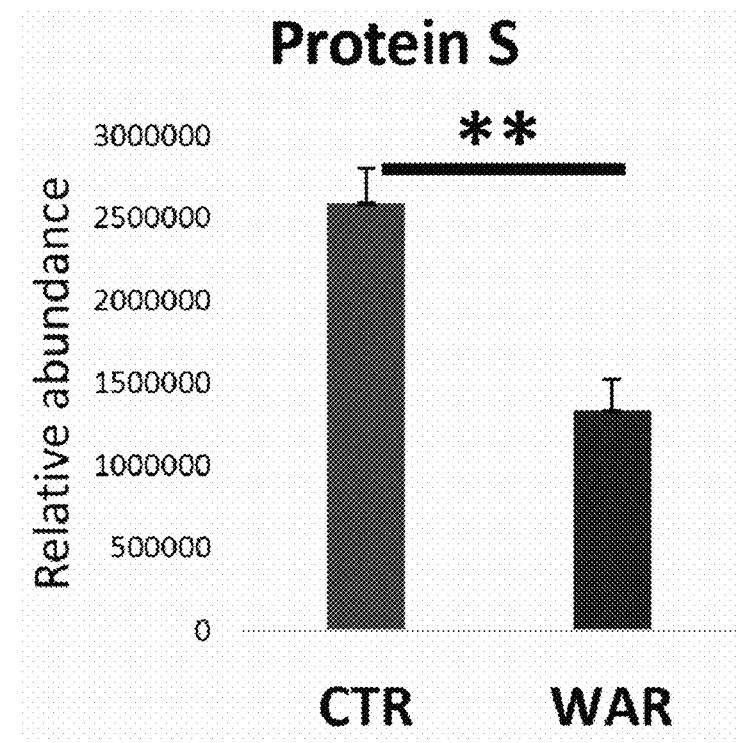
Figure 9D:
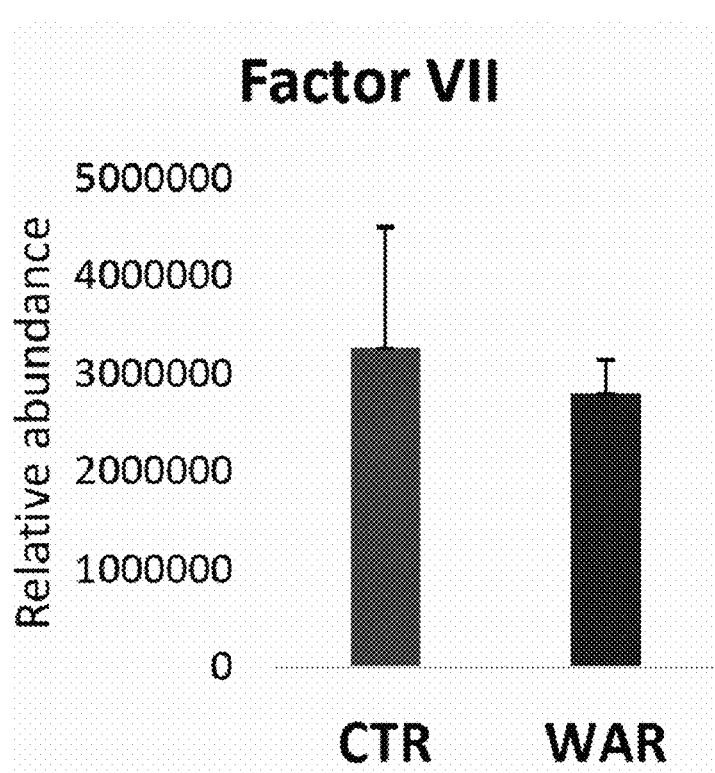
Figure 9E:
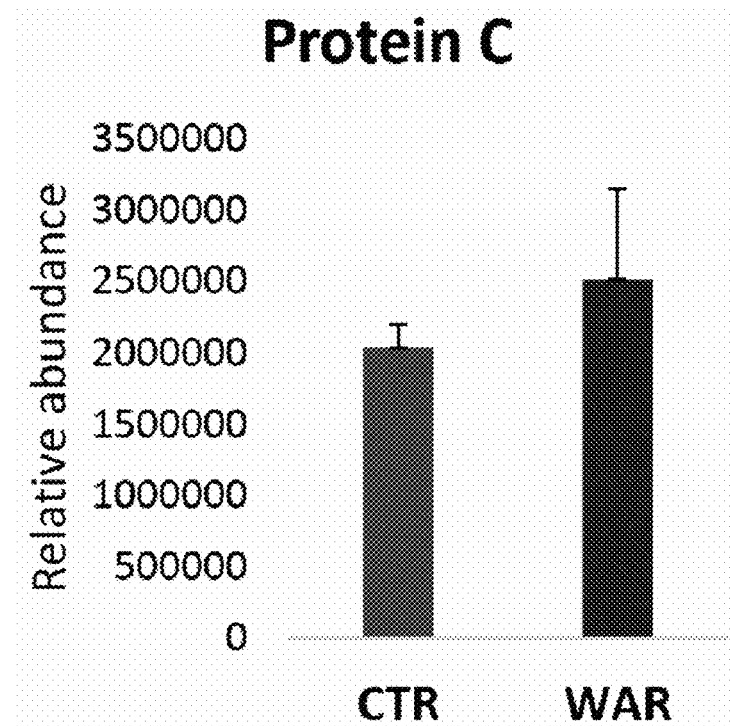
Figure 9F:
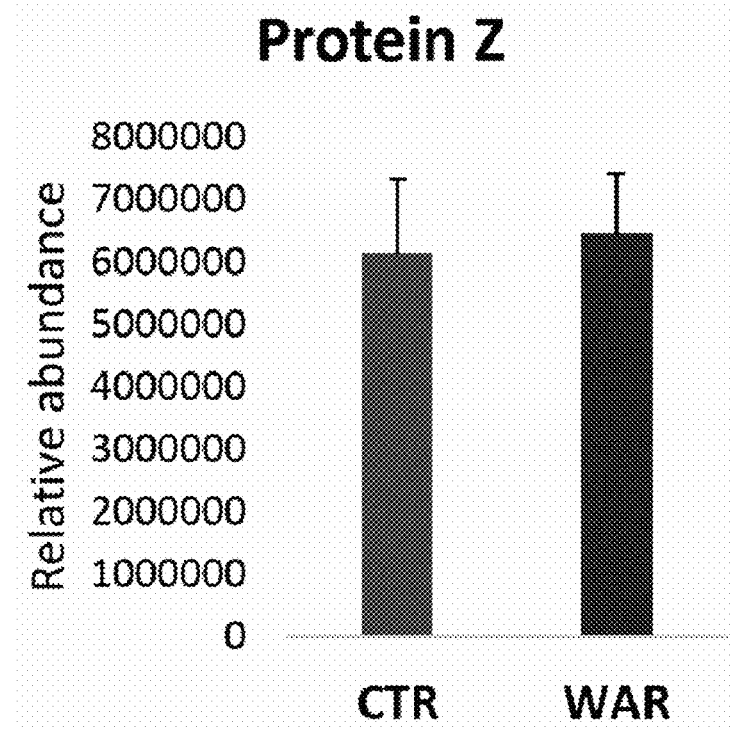

FIG. 9A shows the relative abundance of Factor IX in control samples and warfarin-treated samples. FIG. 9B shows the relative abundance of Factor X in control samples and warfarin-treated samples. FIG. 9C shows the relative abundance of Protein S in control samples and warfarin-treated samples. FIG. 9D shows the relative abundance of Factor VII in control samples and warfarin-treated samples. FIG. 9E shows the relative abundance of Protein C in control samples and warfarin-treated samples. FIG. 9F shows the relative abundance of Protein Z in control samples and warfarin-treated samples.

Figure 10A:
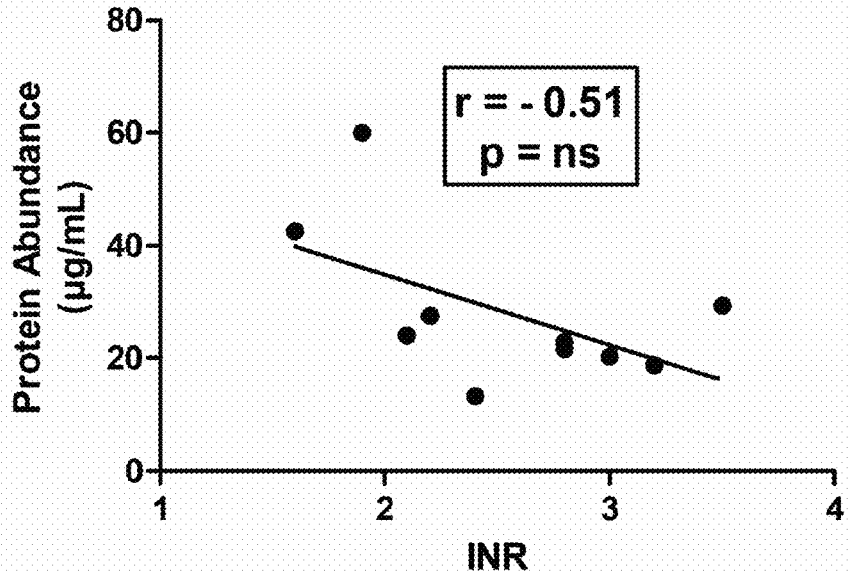
Figure 10B:
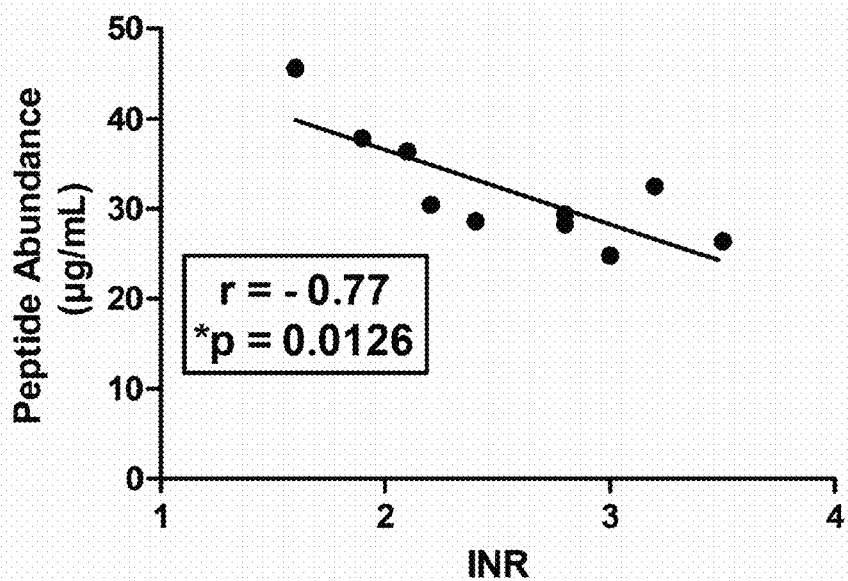
Figure 10C:
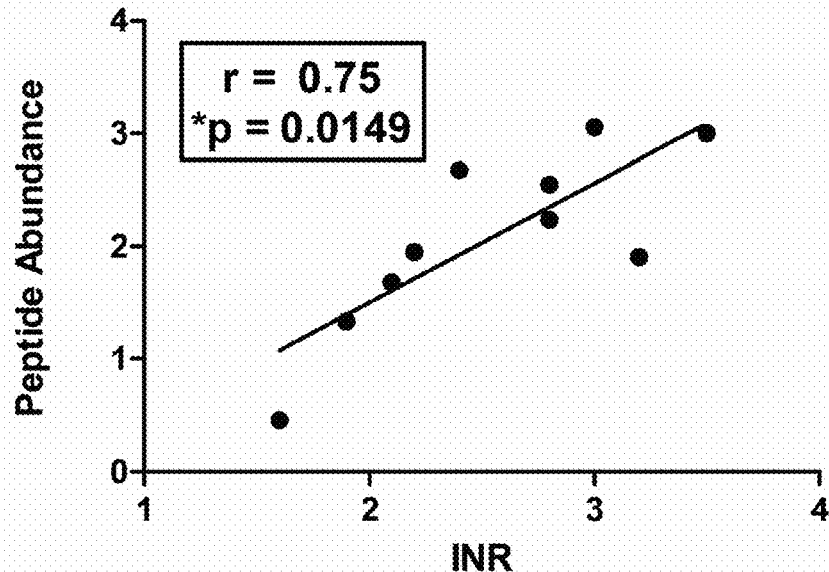
Figure 10D:
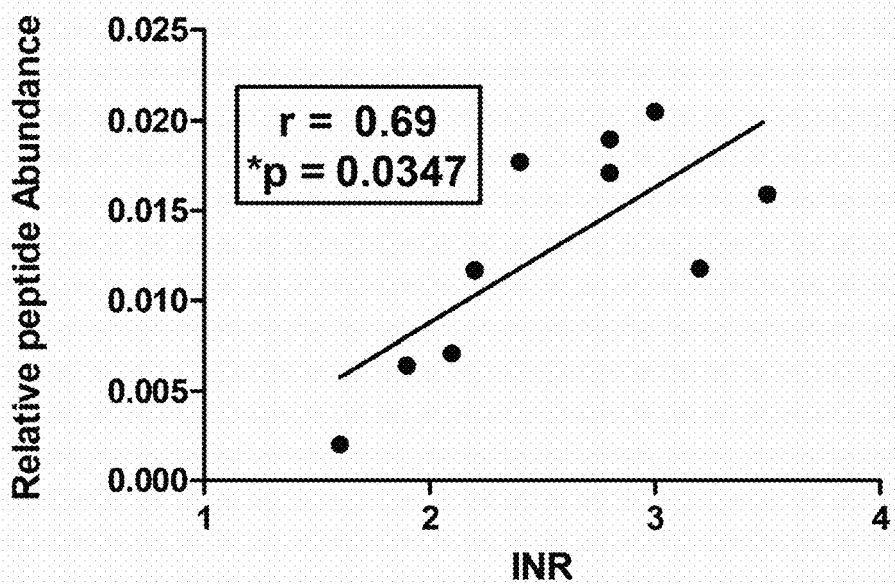
Figure 10E:
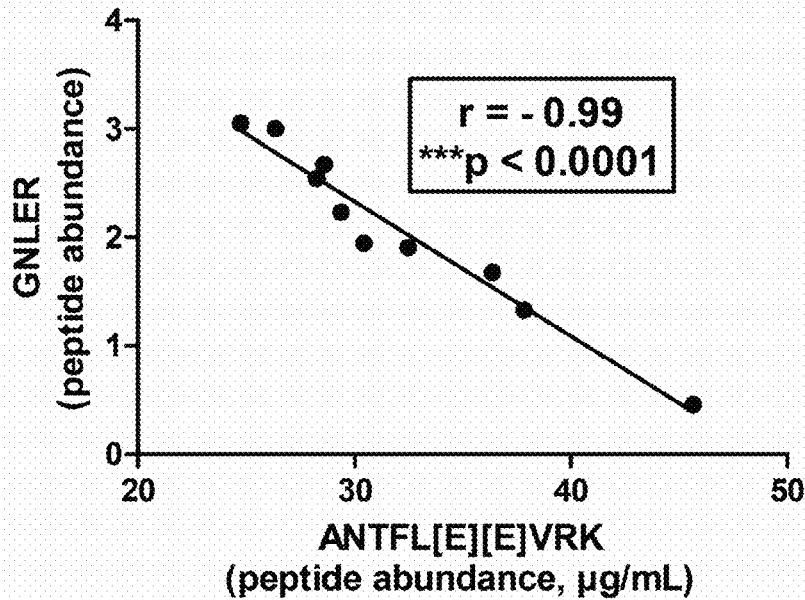
Figure 10F:
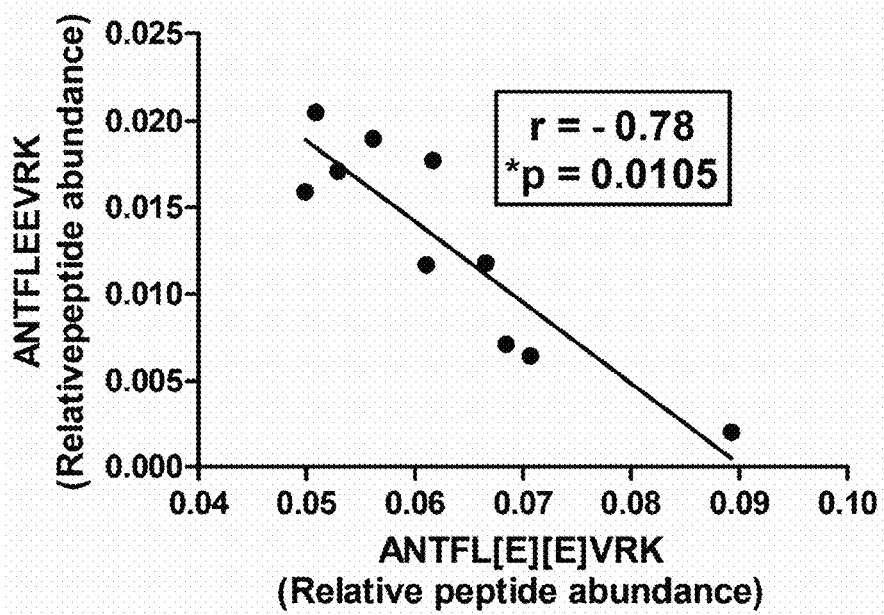

FIG. 10A shows the correlation of INR (International Normalized Ratio of prothrombin time) with the abundance of total prothrombin in serum samples from warfarin-treated subjects (Group 1). FIG. 10B shows the correlation of INR with the abundance of γ-carboxy peptide in serum samples from warfarin-treated subjects (Group 1). FIGS. 10C and 10D show the correlation of INR with the abundance of des-carboxy peptides in serum samples from warfarin-treated subjects (Group 1). FIG. 10E shows the correlation between γ-carboxy peptide ANTFL[E][E]VRK (SEQ ID NO: 5) and des-carboxy peptide GNLER (SEQ ID NO: 6). FIG. 10F shows the correlation between γ-carboxy peptide ANTFL[E][E]VRK (SEQ ID NO: 5) and des-carboxy peptide ANTFLEEVRK (SEQ ID NO: 3).

Figure 11:
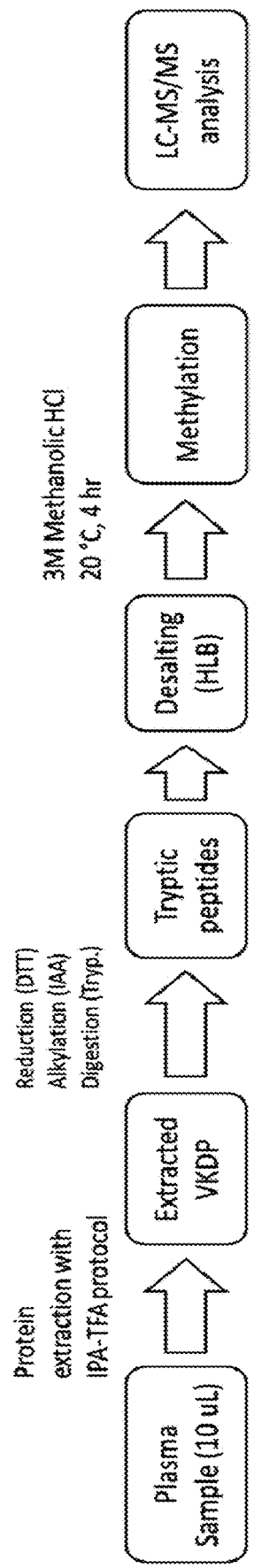

FIG. 11 is a schematic representation of the sample preparation protocol.

DETAILED DESCRIPTION OF THE INVENTION

This disclosure provides a cost-effective and sensitive method for quantification of Gla proteins such as the multiple forms of active and inactive prothrombin. Quantification of Gla proteins is achieved through quantification of one or more of γ-carboxylated proteins, γ-carboxylated protein proteoforms, and des-carboxylated protein, based on determining the quantities of one or more of γ-carboxylated peptides, γ-carboxylated peptide proteoforms, and des-carboxylated peptides. The methods described herein are applicable for titrating anticoagulant therapy and monitoring the impact of diseases such as hepatocellular carcinoma, Sars-CoV-2 (COVID-19), and cancer on clotting physiology.

Proteins which undergo γ-carboxylation are Gla proteins. Gla proteins can be γ-carboxylated at multiple glutamate residues found in a specific protein domain that confers protein activity and is referred to as the Gla domain of the protein. For example, prothrombin undergoes γ-carboxylation at all ten of its glutamic acid, or glutamate, residues in its Gla domain; at least one, but fewer than all, of its glutamic acid or glutamate residues; or none of its glutamic acid or glutamate residues. γ-Carboxylated peptides are portions of these proteins, and comprise a second carboxy group at the glutamic acid, or glutamate, residue gamma carbon atom. γ-Carboxylated peptide proteoforms comprise a γ-carboxyl group on more than one glutamic acid, or glutamate, residue, but does not comprise γ-carboxylation at all glutamic acid, or glutamate, residues in the peptide sequence. Des-carboxylated peptides lack any additional γ-carboxy groups, and are simply glutamic acid- or glutamate-containing peptides.

Figure 1:
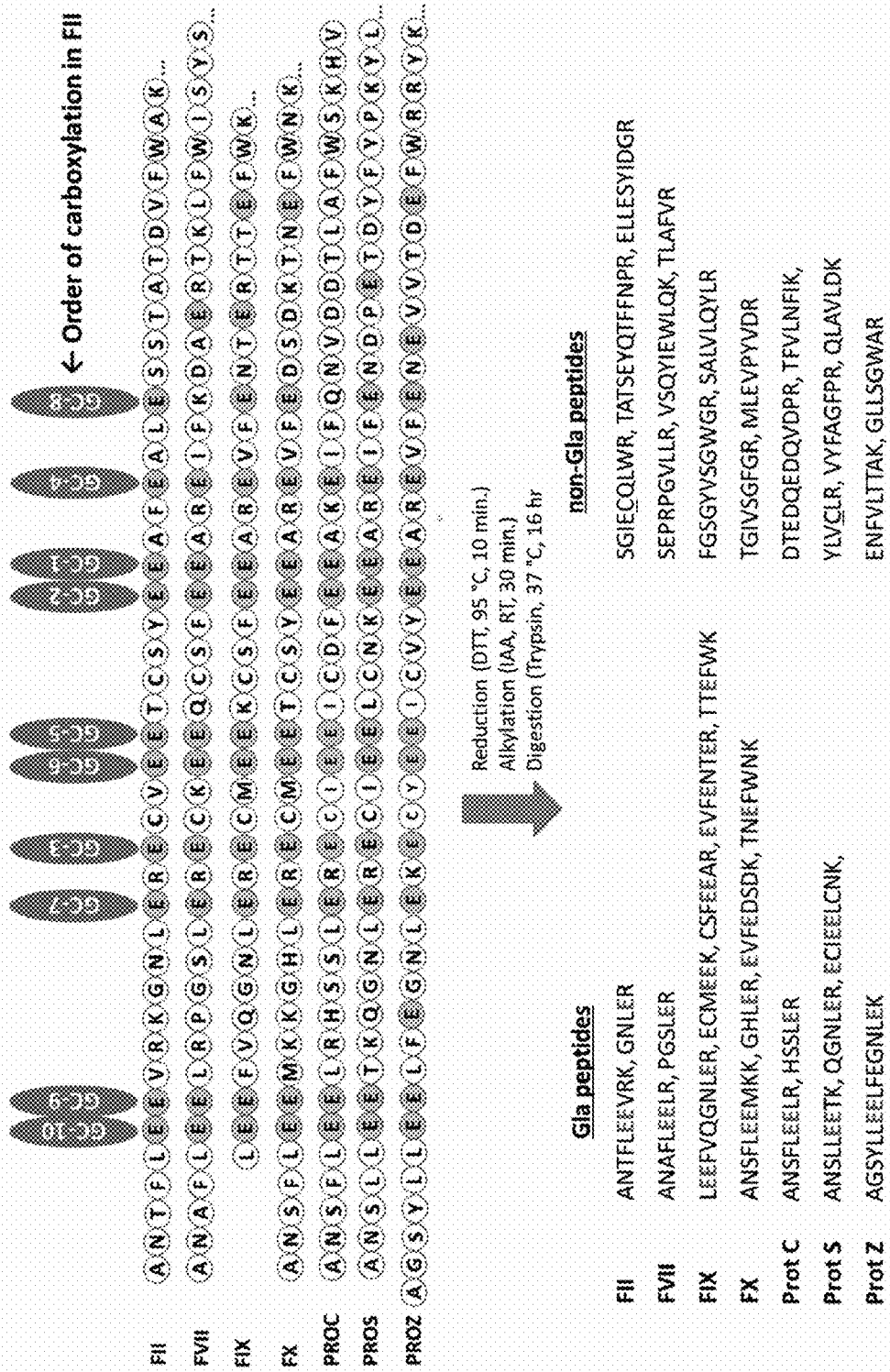
FIG. 1 shows the Gla region of selected vitamin K-dependent proteins.

Carboxylation of the Gla-region peptides is thought to occur sequentially by the order indicated in FIG. 1. Because the most active γ-carboxylated protein proteoforms are γ-carboxylated at positions 9 and 10, the current disclosure has utilized peptides derived from this region of the Gla proteins. This Gla-region comprises two glutamic acid, or glutamate, residues corresponding to the ninth and tenth γ-carboxylation event in each of Factor II, Factor VII, Factor IX, Factor X, Protein C, Protein S, and Protein Z.

Liquid chromatography-mass spectrometry (LC-MS) typically involves separation of analytes (e.g., peptides) based on retention in reversed-phase liquid chromatography (LC) followed by analysis and detection by mass spectrometry (MS). High-resolution MS analyzers such as Orbitrap and time-of-flight (TOF) are employed in protein identification and untargeted quantification using intact protein or peptide information, whereas low-resolution MS analyzers such as quadrupole are useful in targeted analysis of peptides. Tandem mass spectrometry (e.g., triple quadrupole) is used to increase selectivity of LC-MS, where two similar or different analyzers are employed in tandem to selectively detect product ions generated by gas phase fragmentation in a collision induced dissociation (CID) cell. Multiple reaction monitoring (MRM) and selective reaction monitoring (SRM) are the most common targeted proteomics methods which allow selective quantification of unique fragment ions generated from the targeted peptide precursor ion. For example, after separating peptides by LC using optimized conditions (Table 2), the unique precursor-product ion combinations (Table 3) allow selective quantification of peptides of interest. Overall, the MRM approach provides reduced noise level and enhances the signal-to-noise ratio in targeted proteomics.

LC-MS/MS analysis of gamma-carboxy glutamic acid-containing peptides (Gla peptides) is challenging because the peptides undergo neutral loss of $CO_2$ from the γ-carboxy carbon during the collision induced dissociation (CID). This particular property of Gla peptides has hampered the analysis of vitamin K-dependent proteins and there has been no validated quantitative assay or method to analyze these proteins.

As used herein, amino acid residues comprising a γ-carboxyl moiety arising from a γ-carboxylation event are denoted with "[ ]" where, for example, the glutamate or glutamic acid residue which has undergone a γ-carboxylation event and bears two total carboxyl moieties in its side chain is denoted [E].

One aspect of the disclosure provides a method of quantifying an amount of one or more of γ-carboxylated proteins, γ-carboxylated protein proteoforms, and des-carboxylated proteins in a biological sample. The method of the disclosure comprises extracting a sample comprising one or more of γ-carboxylated proteins, γ-carboxylated protein proteoforms, and des-carboxylated proteins from the biological sample having a first concentration, wherein the first concentration can be the concentration of the one or more of γ-carboxylated proteins, γ-carboxylated protein proteoforms, and des-carboxylated proteins as present in a whole blood, plasma, dried blood sample, or other biological sample.

Upon extraction, the one or more of γ-carboxylated proteins, γ-carboxylated protein proteoforms, and des-carboxylated proteins provide a solution having a second concentration, wherein the concentration of the one or more of γ-carboxylated proteins, γ-carboxylated protein proteoforms, and des-carboxylated proteins is greater in the second concentration relative to the other proteins present in the sample, compared with the concentration of the one or more of γ-carboxylated proteins, γ-carboxylated protein proteoforms, and des-carboxylated proteins in the first concentration sample. Such extraction can be achieved by depleting the sample of other abundant proteins, such as by removing serum albumin. Such second concentration provides the advantage of reducing LC-MS/MS ionization suppression as well as reducing high background levels which can result from the presence of highly abundant proteins such as albumin in plasma.

The method of the disclosure additionally comprises contacting the γ-carboxylated proteins, γ-carboxylated protein proteoforms, and des-carboxylated proteins, in the solution having the second concentration, with a protease to effect proteolytic cleavage and provide a solution of peptides comprising one or more of γ-carboxylated peptides, γ-carboxylated peptide proteoforms, and des-carboxylated peptides.

In the method of the disclosure, the quantity of the one or more of γ-carboxylated peptides, γ-carboxylated peptide proteoforms, and des-carboxylated peptides in the solution of peptides is determined. In certain embodiments, the quantity of γ-carboxylated peptides is determined. In other embodiments, the quantity of γ-carboxylated peptide proteoforms is determined. In additional embodiments, the quantity of des-carboxylated peptides is determined. The quantities determined can be an absolute quantity or a relative quantity. The quantities determined can be based on the use of standard proteins or peptides as calibrators, or through the use of standard curves generated for known protein and/or peptide samples.

In embodiments for determining the quantity of the γ-carboxylated peptide proteoforms, the method provides the amount of each proteoform, or one or more proteoforms. For example, Factor II provides ten (10) different Gla peptides (see FIG. 1, GC-1 through GC-10). One Gla peptide is the γ-carboxylated peptide comprising ten γ-carboxylation events (GC-10). One Gla peptide is the des-carboxylated peptide comprising zero (0) γ-carboxylation events. The additional Gla peptides are the γ-carboxylated peptide proteoforms GC-9, GC-8, GC-7, GC-6, GC-5, GC-4, GC-3, GC-2, and GC-1, comprising between nine (9) and one (1) γ-carboxylation events.

In certain embodiments, the method of the invention provides the absolute and/or relative amount of each of one or more of GC-1 through GC-10, and des-carboxylated peptide. In further embodiments, the method of the invention provides the absolute and/or relative amount of each of one or more of GC-1 through GC-10, and des-carboxylated peptide between subjects. Thus, in these embodiments, the method provides a profile of γ-carboxylated peptides, γ-carboxylated peptide proteoforms, and des-carboxylated peptides through determining absolute and/or relative amounts of each peptide to produce the profile. The profile can be used as a diagnostic biomarker for assessing and managing a subject's disease state, such as a subject afflicted with hepatocellular carcinoma (HCC), SARS-CoV-2 (COVID-19), and/or cancer.

In certain embodiments, the method of the invention provides profiles of γ-carboxylated peptides, γ-carboxylated peptide proteoforms, and des-carboxylated peptides from, for example, Factor II, Factor VII, Factor IX, Factor X, Protein C, Protein S, Protein Z, osteocalcin, and/or the calcification-inhibiting matrix Gla protein (MGP).

In certain embodiments, the method of the invention provides profiles of one or more of γ-carboxylated proteins, γ-carboxylated protein proteoforms, and des-carboxylated proteins derived from one or more vitamin K-dependent blood clotting factors, or one or more of γ-carboxylated peptides, γ-carboxylated peptide proteoforms, and des-carboxylated peptides derived from one or more vitamin K-dependent blood clotting factors. In some embodiments, the blood clotting factor is prothrombin (Factor II).

In other embodiments, the method of the disclosure comprises a derivatizing step. In such embodiments, the method comprises quantifying one or more of γ-carboxylated proteins, γ-carboxylated protein proteoforms, and des-carboxylated proteins in a biological sample as described above for extracting the sample and contacting the sample with a protease, and additionally comprising a derivatizing step. In certain embodiments comprising derivatizing, the one or more of γ-carboxylated peptides, γ-carboxylated peptide proteoforms, and des-carboxylated peptides, from the solution of peptides, is/are derivatized to provide one or more derivatized γ-carboxylated peptides, derivatized γ-carboxylated peptide proteoforms, and derivatized des-carboxylated peptides. In other embodiments comprising derivatizing, the one or more of γ-carboxylated peptides and γ-carboxylated peptide proteoforms from the solution of peptides, is/are derivatized to provide one or more derivatized γ-carboxylated peptides and derivatized γ-carboxylated peptide proteoforms.

In further embodiments, derivatization comprises esterification, alkylation, or amidation.

In certain embodiments, the methods comprising derivatizing further comprise determining the quantity of the one or more derivatized γ-carboxylated peptides, derivatized γ-carboxylated peptide proteoforms, and derivatized des-carboxylated peptides, in the solution of derivatized peptides.

In other embodiments, the methods comprising derivatizing further comprise determining the quantity of the one or more derivatized γ-carboxylated peptides and derivatized γ-carboxylated peptide proteoforms in the solution of derivatized peptides. In such embodiments, the quantified des-carboxylated peptide is not derivatized.

In the method of the disclosure, the quantity of the one or more derivatized γ-carboxylated peptides, derivatized γ-carboxylated peptide proteoforms, and derivatized des-carboxylated peptides in the solution of peptides is/are determined. In other embodiments, the quantity of derivatized γ-carboxylated peptides and derivatized γ-carboxylated peptide proteoforms is determined. In certain embodiments, the quantity of derivatized γ-carboxylated peptides is determined. In other embodiments, the quantity of derivatized γ-carboxylated peptide proteoforms is determined. In additional embodiments, the quantity of derivatized des-carboxylated peptides is determined. The quantity of derivatized peptides determined can be an absolute quantity or a relative quantity. The quantity determined can be based on the use of standard proteins or peptides as calibrators, or through the use of standard curves generated for known protein and/or peptide samples.

In embodiments for determining the quantity of the derivatized γ-carboxylated peptide proteoforms, the method provides the amount of each proteoform, or one or more proteoforms. For example, Factor II provides ten (10) different Gla peptides (see FIG. 1, GC-1 through GC-10). The quantity of one or more of γ-carboxylated peptide proteoforms GC-9, GC-8, GC-7, GC-6, GC-5, GC-4, GC-3, GC-2, and GC-1, comprising between nine (9) and one (1) γ-carboxylation events is determined by quantifying one or more of the γ-carboxylated peptide proteoforms as derivatized γ-carboxylated peptide proteoforms.

In certain embodiments, the method comprises determining the quantity of one or more of derivatized γ-carboxylated peptides and derivatized γ-carboxylated peptide proteoforms GC-10, GC-9, GC-8, GC-7, GC-6, GC-5, GC-4, GC-3, GC-2, GC-1 as well as derivatized des-carboxylated peptides. In other embodiments, the method comprises determining the quantity of one or more derivatized γ-carboxylated peptides and derivatized γ-carboxylated peptide proteoforms GC-10, GC-9, GC-8, GC-7, GC-6, GC-5, GC-4, GC-3, GC-2, GC-1, as well as underivatized des-carboxylated peptides.

In certain embodiments, the method of the invention provides the absolute and/or relative amount of each of one or more derivatized GC-1 through GC-10, and des-carboxylated peptide. In further embodiments, the method of the invention provides the absolute and/or relative amount of each of one or more derivatized GC-1 through GC-10, and des-carboxylated peptide between subjects. In certain embodiments, the method provides a profile of one or more derivatized γ-carboxylated peptides, derivatized γ-carboxylated peptide proteoforms, and derivatized des-carboxylated peptides through determining absolute and/or relative amounts of each derivatized peptide to produce the profile. In other embodiments, the method provides a profile of one or more derivatized γ-carboxylated peptides, derivatized γ-carboxylated peptide proteoforms, and underivatized des-carboxylated peptides through determining absolute and/or relative amounts of each peptide to produce the profile. The profile can be used as a diagnostic biomarker for assessing and managing a subject's disease state, such as a subject afflicted with hepatocellular carcinoma (HCC), SARS-CoV-2 (COVID-19), and/or cancer.

In certain embodiments, the method of the invention provides profiles of one or more derivatized γ-carboxylated peptides, derivatized γ-carboxylated peptide proteoforms, and derivatized des-carboxylated peptides from, for example, Factor II, Factor VII, Factor IX, Factor X, Protein C, Protein S, Protein Z, osteocalcin, and/or the calcification-inhibiting matrix Gla protein (MGP). In other embodiments, the method of the invention provides profiles of one or more derivatized γ-carboxylated peptides, derivatized γ-carboxylated peptide proteoforms, and underivatized des-carboxylated peptides from, for example, Factor II, Factor VII, Factor IX, Factor X, Protein C, Protein S, Protein Z, osteocalcin, and/or the calcification-inhibiting matrix Gla protein (MGP).

In certain embodiments, the method of the invention provides profiles of one or more derivatized γ-carboxylated peptides, derivatized γ-carboxylated peptide proteoforms, and derivatized des-carboxylated peptides derived from one or more vitamin K-dependent blood clotting factors. In other embodiments, the method of the invention provides profiles of one or more derivatized γ-carboxylated peptides, derivatized γ-carboxylated peptide proteoforms, and underivatized des-carboxylated peptides, derived from one or more vitamin K-dependent blood clotting factors. In certain embodiments, the blood clotting factor is prothrombin (Factor II).

In certain embodiments, the method comprises determining the quantity of non-Gla region proteins or peptides. In such embodiments, the quantity of non-Gla region proteins or peptides can be used to determine total Gla protein content of a biological sample.

The method of quantifying an amount of one or more of γ-carboxylated peptides, γ-carboxylated peptide proteoforms, and des-carboxylated peptides, or one or more of derivatized γ-carboxylated peptides, derivatized γ-carboxylated peptide proteoforms, and derivatized des-carboxylated peptides in a sample comprises mass spectrometric analysis. In embodiments comprising mass spectrometric analysis, the method can comprise a combination of one or more of γ-carboxylated peptides, γ-carboxylated peptide proteoforms, and des-carboxylated peptides, with one or more derivatized γ-carboxylated peptides, derivatized γ-carboxylated peptide proteoforms, and derivatized des-carboxylated peptides.

In a further embodiment, mass spectrometric analysis comprises tandem mass spectrometric (MS/MS) analysis.

Mass spectrometric analysis and/or tandem mass spectrometric analysis can comprise mass spectrometric techniques such as electrospray ionization (ESI), quadrupole, time of flight (TOF), Orbitrap, other mass spectrometric techniques known in the art.

In further embodiments, the mass spectrometric analysis comprises liquid chromatographic mass spectrometric (LC-MS) analysis and/or liquid chromatographic tandem mass spectrometric analysis (LC-MS/MS).

In further embodiments, the mass spectrometric analysis comprises multiple reaction monitoring (MRM) of a fragmentation profile of the one or more of γ-carboxylated peptides, γ-carboxylated peptide proteoforms, and des-carboxylated peptides, or derivatized γ-carboxylated peptides, derivatized γ-carboxylated peptide proteoforms, and derivatized des-carboxylated peptides. In embodiments comprising multiple reaction monitoring (MRM) of a fragmentation profile, the method can comprise a combination of one or more of γ-carboxylated peptides, γ-carboxylated peptide proteoforms, and des-carboxylated peptides, with one or more derivatized γ-carboxylated peptides, derivatized γ-carboxylated peptide proteoforms, and derivatized des-carboxylated peptides.

The method of determining a peptide quantity or profile utilizing multiple reaction monitoring (MRM) comprises comparing the peak intensities of the peptide fragment ions with light external calibrator or internal standard fragment ions to determine the amount of the one or more γ-carboxylated peptides, γ-carboxylated peptide proteoforms, and des-carboxylated peptides; one or more derivatized γ-carboxylated peptides, derivatized γ-carboxylated peptide proteoforms, and derivatized des-carboxylated peptides; or a combination of such derivatized peptides with such underivatized peptides.

Any suitable Gla protein can be quantified or monitored by the method of the disclosure. In certain embodiments, the one or more of γ-carboxylated peptides, γ-carboxylated peptide proteoforms, and des-carboxylated peptides is/are derived from prothrombin (Factor II), Factor VII, Factor IX, Factor X, the anticoagulant proteins C and S, the factor X-targeting protein Z, osteocalcin, the calcification-inhibiting matrix Gla protein (MGP), the growth arrest specific gene 6 protein (GAS6), periostin, transmembrane Gla proteins (TMGPs), transthyretin (thyroxin binding protein), and/or proline-rich Gla-proteins (PRGPs). In other embodiments, the or one or more derivatized γ-carboxylated peptides, derivatized γ-carboxylated peptide proteoforms, and derivatized des-carboxylated peptides is/are derived from prothrombin (Factor II), Factor VII, Factor IX, Factor X, the anticoagulant proteins C and S, the factor X-targeting protein Z, osteocalcin, the calcification-inhibiting matrix Gla protein (MGP), the growth arrest specific gene 6 protein (GAS6), periostin, transmembrane Gla proteins (TMGPs), transthyretin (thyroxin binding protein), and/or proline-rich Gla-proteins (PRGPs). In other embodiments, the peptides derived from prothrombin (Factor II), Factor VII, Factor IX, Factor X, the anticoagulant proteins C and S, the factor X-targeting protein Z, osteocalcin, the calcification-inhibiting matrix Gla protein (MGP), the growth arrest specific gene 6 protein (GAS6), periostin, transmembrane Gla proteins (TMGPs), transthyretin (thyroxin binding protein), and/or proline-rich Gla-proteins (PRGPs) can comprise a combination of derivatized and un-derivatized peptides.

In certain embodiments, the sample is plasma, serum, or blood. In a further embodiment, the sample is plasma. Any type of blood sample can be used with the methods of the disclosure, including venous, capillary, and arterial blood. In certain embodiments, the blood sample is a dried blood spot (DBS). A blood sample, such as a dried blood spot, can be collected from a patient in one location and shipped to a different location, such as a reference laboratory, for analysis using a method of the disclosure. Any dried blood spot can be used with the methods of the disclosure. For example, a dried blood spot can be derived from a sample obtained from a heel prick, a finger prick, or any other appropriate manner. In certain embodiments, the sample can be self-collected by the patient in need of the quantification of one or more Gla proteins.

The methods of the disclosure require small sample volumes. In certain embodiments, the plasma, serum, or blood sample has a volume as little as about 5 uL to about 100 uL, about 5 uL to about 50 uL, about 5 uL to about 30 uL, about 5 uL to about 20 uL, or about 10 uL to about 20 uL. In some embodiments, the sample has a volume of about 10 uL. In some embodiments, the dried blood spot is a dried blood spot obtained from a blood sample having a volume of about 5 uL to about 100 uL, about 5 uL to about 50 uL, about 5 uL to about 30 uL, about 5 uL to about 20 uL, or about 10 uL to about 20 uL. In certain embodiments, the blood spot can be obtained from a larger blood sample, and a part of the blood spot corresponding to a liquid volume of about 5 uL to about 50 uL can be used to prepare a sample for the method of the disclosure. In certain embodiments, the dried blood spot is reconstituted prior to analysis to obtain an aqueous sample comprising proteins and/or peptides.

In certain embodiments, the methods can be used to quantify one or more vitamin K-dependent proteins, such as one or more blood clotting factors. In further embodiments, the one or more blood clotting factors is prothrombin (Factor II).

In certain embodiments, the proteins in the sample are digested or proteolytically cleaved using one or more proteases. In further embodiments, the proteolytic cleavage comprises contacting the sample with trypsin or chymotrypsin.

In certain embodiments, the one or more of γ-carboxylated peptides comprises peptides comprising the following sequences: ANTFL[E][E]VRK (SEQ ID NO: 5) and GNL[E]R (SEQ ID NO: 7) for prothrombin; ANAFL[E][E]LRPGSL[E]R (SEQ ID NO: 8), [E]IFKDA[E]R (SEQ ID NO: 9), and PGSL[E]R (SEQ ID NO: 51) for Factor VII; L[E][E]FVQGNL[E]R (SEQ ID NO: 10), [E]CM[E][E]K (SEQ ID NO: 11), CSF[E][E]AR (SEQ ID NO: 12), [E]VF[E]NT[E]R (SEQ ID NO: 13) and TT[E]FWK (SEQ ID NO: 14) for Factor IX; ANSFL[E][E]MK (SEQ ID NO: 1), [E]VF[E]DSDK (SEQ ID NO: 15), TN[E]FWNK (SEQ ID NO: 16), and GHL[E]R (SEQ ID NO: 59) for Factor X; ANSLL[E][E]TK (SEQ ID NO: 17), QGNL[E]R (SEQ ID NO: 18) and [E]CI[E][E]LCNK (SEQ ID NO: 19) for Protein S; ANSFL[E][E]LR (SEQ ID NO: 20), HSSL[E]R (SEQ ID NO: 21) and [E]IFQNVDDTLAFWSK (SEQ ID NO: 22) for Protein C; YLYQWLGAPVPYPDPL[E]PR (SEQ ID NO: 23) and [E]VC[E]LNPDCD[E]LADHIGFQ[E]AYR (SEQ ID NO: 24) for osteocalcin; SKPVH[E]LNR (SEQ ID NO: 25) and [E]ACDDYR (SEQ ID NO: 26) for matrix Gla protein (MGP).

In certain embodiments, the one or more of des-carboxylated peptides comprises peptides comprising the following sequences: ANTFLEEVRK (SEQ ID NO: 3) and GNLER (SEQ ID NO: 6) for prothrombin; ANFLEELRPGSLER (SEQ ID NO: 27), EIFKDAER (SEQ ID NO: 28), and PGSLER (SEQ ID NO: 53) for Factor VII; LEEFVQGNLER (SEQ ID NO: 29), ECMEEK (SEQ ID NO: 30), CSFEEAR (SEQ ID NO: 31), EVFENTER (SEQ ID NO: 32) and TTEFWK (SEQ ID NO: 33) for Factor IX; ANSFLEEMK (SEQ ID NO: 34), EVFEDSDK (SEQ ID NO: 35), TNEFWNK (SEQ ID NO: 36), and GHLER (SEQ ID NO: 60) for Factor X; ANSLLEETK (SEQ ID NO: 37), QGNLER (SEQ ID NO: 38) and ECIEELCNK (SEQ ID NO: 39) for Protein S; ANSFLEELR (SEQ ID NO: 40), HSSLER (SEQ ID NO: 41) and EIFQNVDDTLAFWSK (SEQ ID NO: 42) for Protein C; YLYQWLGAPVPYPDPLEPR (SEQ ID NO: 43) and EVCELNPDCDELADHIGFQEAYR (SEQ ID NO: 44) for osteocalcin; and SKPVHELNR (SEQ ID NO: 45) and EACDDYR (SEQ ID NO: 46) for MGP.

Table 1 below provides a list of peptides from the Gla and non-Gla regions of vitamin K-dependent proteins quantifiable using the disclosed method.

TABLE 1

| Protein | Protein region | Peptides |
|---|---|---|
| FII | Gla-Carboxy | ANTFL[E][E]VRK (SEQ ID NO: 5); GNL[E]R (SEQ ID NO: 7) |
| | Gla-Descarboxy | ANTFLEEVRK (SEQ ID NO: 3); GNLER (SEQ ID NO: 6) |

TABLE 1-continued

| Protein | Protein region | Peptides |
|---|---|---|
| | non-Gla | SGIECQLWR (SEQ ID NO: 47); TATSEYQTFFNPR (SEQ ID NO: 48); ELLESYIDGR (SEQ ID NO: 49) |
| FVII | Gla-Carboxy | ANAFL[E][E]LR (SEQ ID NO: 50); PGSL[E]R (SEQ ID NO: 51) |
| | Gla-Descarboxy | ANAFLEELR (SEQ ID NO: 52); PGSLER (SEQ ID NO: 53) |
| | non-Gla | SEPRPGVLLR (SEQ ID NO: 54); VSQYIEWLQK (SEQ ID NO: 55); TLAFVR (SEQ ID NO: 56) |
| FIX | Gla-Carboxy | L[E][E]FVQGNL[E]R (SEQ ID NO: 10); [E]CM[E][E]K (SEQ ID NO: 11); CSF[E][E]AR (SEQ ID NO: 12); [E]VF[E]NT[E]R (SEQ ID NO: 13); TT[E]FWK (SEQ ID NO: 14) |
| | Gla-Descarboxy | LEEFVQGNLER (SEQ ID NO: 29); ECMEEK (SEQ ID NO: 30); CSFEEAR (SEQ ID NO: 31); EVFENTER (SEQ ID NO: 32); TTEFWK (SEQ ID NO: 33) |
| | non-Gla | FGSGYVSGWGR (SEQ ID NO: 57); SALVLQYLR (SEQ ID NO: 58) |
| FX | Gla-Carboxy | ANSFL[E][E]MKK (SEQ ID NO: 1); GHL[E]R (SEQ ID NO: 59); [E]VF[E]DSDK (SEQ ID NO: 15); TN[E]FWNK (SEQ ID NO: 16) |
| | Gla-Descarboxy | ANSFLEEMKK (SEQ ID NO: 34); GHLER (SEQ ID NO: 60); EVFEDSDK (SEQ ID NO: 35); TNEFWNK (SEQ ID NO: 36) |
| | non-Gla | TGIVSGFGR (SEQ ID NO: 61); MLEVPYVDR (SEQ ID NO: 62) |
| Protein C | Gla-Carboxy | ANSFL[E][E]LR (SEQ ID NO: 20); HSSL[E]R (SEQ ID NO: 21) |
| | Gla-Descarboxy | ANSFLEELR (SEQ ID NO: 40); HSSLER (SEQ ID NO: 41) |
| | non-Gla | DTEDQEDQVDPR (SEQ ID NO: 63); TFVLNFIK (SEQ ID NO: 64) |
| Protein S | Gla-Carboxy | ANSLL[E][E]TK (SEQ ID NO: 17); QGNL[E]R (SEQ ID NO: 18); [E]CI[E][E]LCNK (SEQ ID NO: 19) |
| | Gla-Descarboxy | ANSLLEETK (SEQ ID NO: 37); QGNLER (SEQ ID NO: 38); ECIEELCNK (SEQ ID NO: 39) |
| | non-Gla | YLVCLR (SEQ ID NO: 65); VYFAGFPPR (SEQ ID NO: 66); QLAVLDK (SEQ ID NO: 67) |
| Protein Z | Gla-Carboxy | AGSYLL[E][E]LF[E]GNL[E]K (SEQ ID NO: 68) |
| | Gla-Descarboxy | AGSYLLEELFEGNLEK (SEQ ID NO: 69) |
| | non-Gla | ENFVLTTAK (SEQ ID NO: 70); GLLSGWAR (SEQ ID NO: 71) |

In embodiments comprising one or more of γ-carboxylated peptide proteoforms or one or more derivatized γ-carboxylated peptide proteoforms, at least one glutamate, or glutamic acid, residue is γ-carboxylated, and fewer than all glutamate, or glutamic acid, residues are γ-carboxylated.

In another embodiment, the disclosure provides a method for administering an anticoagulant to a subject in need thereof. Such embodiments comprise obtaining a sample from a patient as described herein, and subsequently determining the quantity of one or more of γ-carboxylated peptides, γ-carboxylated peptide proteoforms, and des-carboxylated peptides, or one or more derivatized γ-carboxylated peptides, derivatized γ-carboxylated peptide proteoforms, and derivatized des-carboxylated peptides. Optionally, the method comprises determining the quantity of a combination of derivatized peptides and underivatized peptides. The method further comprises determining a therapeutically effective dose of an anticoagulant to be administered based on the quantity of one or more of γ-carboxylated peptides, γ-carboxylated peptide proteoforms, and des-carboxylated peptides; one or more derivatized γ-carboxylated peptides, derivatized γ-carboxylated peptide proteoforms, and derivatized des-carboxylated peptides; or the quantity of a combination of derivatized peptides and underivatized peptides, wherein a correlation is determined between the peptide quantity and dose of anticoagulant to be administered. The method additionally further comprises administering the therapeutically effective dose of the anticoagulant to the subject.

In embodiments comprising an anticoagulant, the anticoagulant is a vitamin K pathway inhibitor. In embodiments comprising an anticoagulant, the anticoagulant is warfarin, dabigatran, rivaroxaban, apixaban, betrixaban, or edoxaban. The disclosed method is particularly suitable for administration of an anticoagulant with a narrow therapeutic window, wherein the range of anticoagulant which can be administered is small.

Any suitable sample can be used for determining the quantity of one or more of γ-carboxylated peptides, γ-carboxylated peptide proteoforms, and des-carboxylated peptides; one or more derivatized γ-carboxylated peptides, derivatized γ-carboxylated peptide proteoforms, and derivatized des-carboxylated peptides; or a combination of derivatized peptides and underivatized peptides. For example, the sample can be plasma, serum, blood, or a dried blood spot, such as those described above. In certain embodiments, the subject suffers from a blood-clotting disorder.

In another embodiment, the disclosure provides a method for diagnosing hepatocellular carcinoma (HCC) in a subject. Diagnosing HCC comprises determining the quantity of one or more of γ-carboxylated peptides, γ-carboxylated peptide proteoforms, and des-carboxylated peptides; determining the quantity of one or more derivatized γ-carboxylated peptides, derivatized γ-carboxylated peptide proteoforms, and derivatized des-carboxylated peptides; or determining the quantity of a combination of derivatized peptides and underivatized peptides. The method further comprises comparing the quantity of one or more peptides from a subject with a quantity of one or more peptides obtained from a control sample. For example, the method can comprise comparing the quantity of one or more of γ-carboxylated peptides, γ-carboxylated peptide proteoforms, and des-carboxylated peptides from a subject with a quantity of one or more of γ-carboxylated peptides, γ-carboxylated peptide proteoforms, and des-carboxylated peptides from a control sample. In another embodiment, the method comprises comparing the quantity of one or more derivatized γ-carboxylated peptides, derivatized γ-carboxylated peptide proteoforms, and derivatized des-carboxylated peptides with a quantity of one or more derivatized γ-carboxylated peptides, derivatized γ-carboxylated peptide proteoforms, and derivatized des-carboxylated peptides obtained from a control sample. In another embodiment, the method comprises comparing the quantity of one or more derivatized γ-carboxylated peptides, derivatized γ-carboxylated peptide proteoforms, and underivatized des-carboxylated peptides with a quantity of one or more derivatized γ-carboxylated peptides, derivatized γ-carboxylated peptide proteoforms, and underivatized des-carboxylated peptides obtained from a control sample.

In a subject afflicted with HCC, the quantity of des-carboxylated peptides or proteins is greater than the quantity of des-carboxylated peptides or proteins in a control sample. Additionally, in a subject afflicted with HCC, the quantity of γ-carboxylated peptides or proteins is less than the quantity of γ-carboxylated peptides or proteins in a control sample. In certain embodiments, such peptides measured can be measured as derivatized peptides. A difference between such quantified amounts of peptides between a subject and a control sample can be assessed. The difference can be compared to a predetermined threshold value. A difference between the quantified amounts greater than the predetermined threshold is diagnostic of HCC. The above method is applicable for diagnosis and management of HCC, as supported by the literature. See Sun, X., et al. BMC Cancer 21(1):775, July 2021 and Bhatti, A., et al. Asian Pac. J. Cancer Prev. 22(6):1731-1736, June 2021.

In embodiments comprising one or more of γ-carboxylated peptides, γ-carboxylated peptide proteoforms, and des-carboxylated peptides; one or more derivatized γ-carboxylated peptides, derivatized γ-carboxylated peptide proteoforms, and derivatized des-carboxylated peptides; or a combination of derivatized peptides and underivatized peptides, the peptides are derived from prothrombin (Factor II).

As used herein, the term "about" indicates that the subject value can be modified by 5% more, or 5% less, and still fall within the disclosed embodiment.

The following examples are provided for the purpose of illustrating, not limiting, the invention.

Sample Procurement

The plasma samples were collected from two groups. Group 1 consisted of 12 individuals receiving antithrombotic warfarin therapy. Group 2 consisted of 12 healthy adults not receiving antithrombotic warfarin therapy, and comprised the control samples. The samples comprised venous blood (4.5 mL), which was collected by venipuncture from a peripheral arm vein into a tube containing sodium citrate. Aliquots were removed for whole blood prothrombin time measurement and INR determination. After sedimentation of blood cells from the remaining blood by centrifugation at 10,000×g, the plasma was removed and stored at 4° C. and then at −80° C. before LC-MS/MS analysis of the Gla proteins.

Gla Protein Extraction

The isolated plasma sample containing the γ-carboxylated proteins, γ-carboxylated protein proteoforms, and/or des-carboxylated proteins was concentrated by depleting serum albumin from the plasma sample. A 10 μL plasma sample was used for Gla protein extraction. To achieve concentration, ten volumes of 0.1% TFA in IPA was vortex-mixed with the plasma sample for 2 min and then centrifuged at 1500×g, for 5 min at 4° C. The resulting supernatant containing the albumin was discarded. The pellet was retained.

Gla Peptide Formation

The concentrated plasma sample pellet from the Gla protein extraction was treated as follows. Ninety-five μL of the extracted protein in 4% SDS:ABC (1:1, v/v) was denatured and reduced using 30 μL ammonium bicarbonate (ABC, 100 mM) and 10 μL of 250 mM dithiothreitol (DTT) at 95° C. for 10 min with gentle shaking at 300 rpm. The sample was cooled at room temperature for 10 min, and subsequently alkylated with 20 μL of 500 mM iodoacetamide (IAA) in the dark for 30 min. Ice-cold methanol-chloroform (600 μL, 5:1 v/v) and water (400 μL) were subsequently added. After vortex-mixing and centrifugation at 16,000×g (4° C.) for 5 min, the upper aqueous and lower organic layers were carefully removed without disturbing the protein pellet, using vacuum suction. The protein pellet was dried at room temperature for 10 min and then washed with 500 μL ice-cold methanol, followed by centrifugation at 8000×g (4° C.) for 5 min. The supernatant was removed. The remaining pellet was dried at room temperature for 30 min and re-suspended in 60 μL of ammonium bicarbonate buffer (50 mM, pH 7.8). The protein pellet was then digested, or proteolytically cleaved, by adding 20 μL of the protease trypsin (protein:trypsin ratio, approximately 100:1) and incubating at 37° C. for 16 hours. The reaction was quenched by the addition of 20 μL of peptide internal standard cocktail (prepared in 80% acetonitrile in water containing 0.5% formic acid). The sample was mixed by vortex mixing and then centrifuged at 8000×g for 5 min. The supernatant containing one or more of γ-carboxylated peptides, γ-carboxylated peptide proteoforms, and des-carboxylated peptides was collected.

Peptide Derivatization

Figure 2:
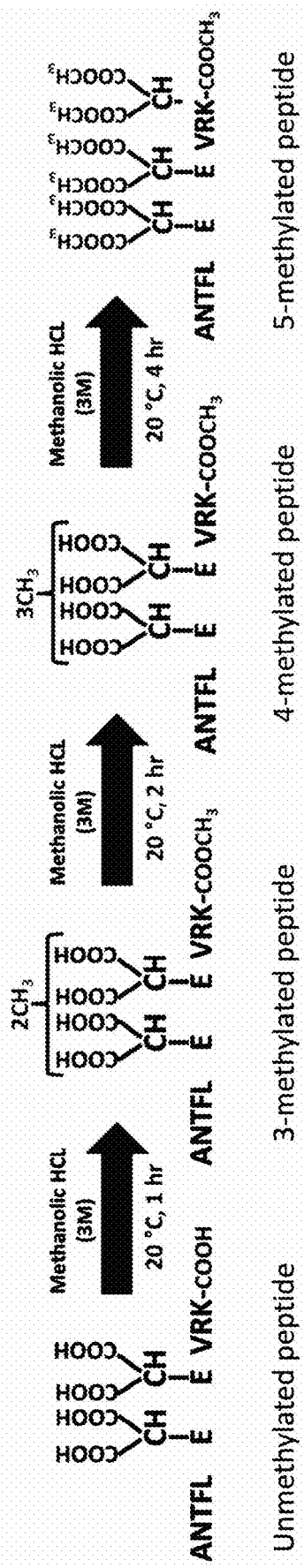
FIG. 2 shows the methyl ester formation reaction scheme.

An aliquot of the digested, or proteolytically cleaved, protein sample containing the pool of peptides was desalted with optimized solid phase extraction protocol. This sample of digested, or proteolytically cleaved, peptides was diluted with 0.2% formic acid (1 mL). The hydrophilic lipophilic balance (HLB) cartridges (Waters, Milford, MA) were conditioned with acetonitrile (1 mL) followed by equilibration with 0.2% formic acid (1 mL). The sample was then loaded onto the HLB cartridges and the polar sample content was washed with 0.2% formic acid. The peptides were eluted with 0.5 mL acetonitrile into a glass vial. The eluent was evaporated with nitrogen and the dried residue containing peptides was treated with 3M methanolic HCl, incubated 4 hours, at 20° C., as shown in the reaction scheme in FIG. 2. The reaction was quenched by evaporation of methanolic HCl under nitrogen for 20 min at 37° C. The derivatization process yielded methyl ester derivatives of the carboxylic acid moieties of the one or more of γ-carboxylated peptides and γ-carboxylated peptide proteoforms, as well as any other carboxylic acid-containing peptide residues also present in the mixture.

Figure 3A:
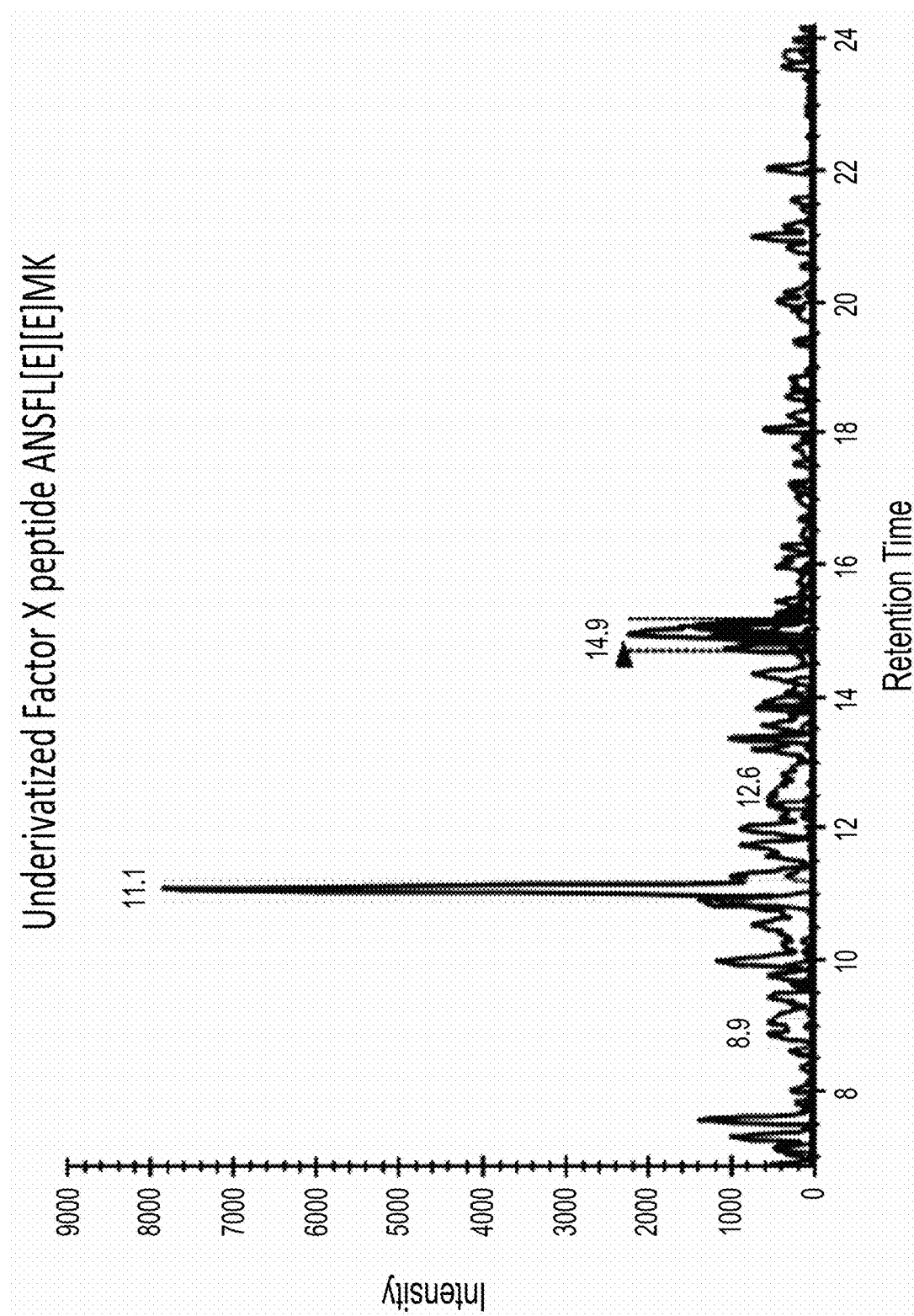
FIG. 3A shows the liquid chromatographic profile of ANSFL[E][E]MK (SEQ ID NO: 1).
Figure 3B:
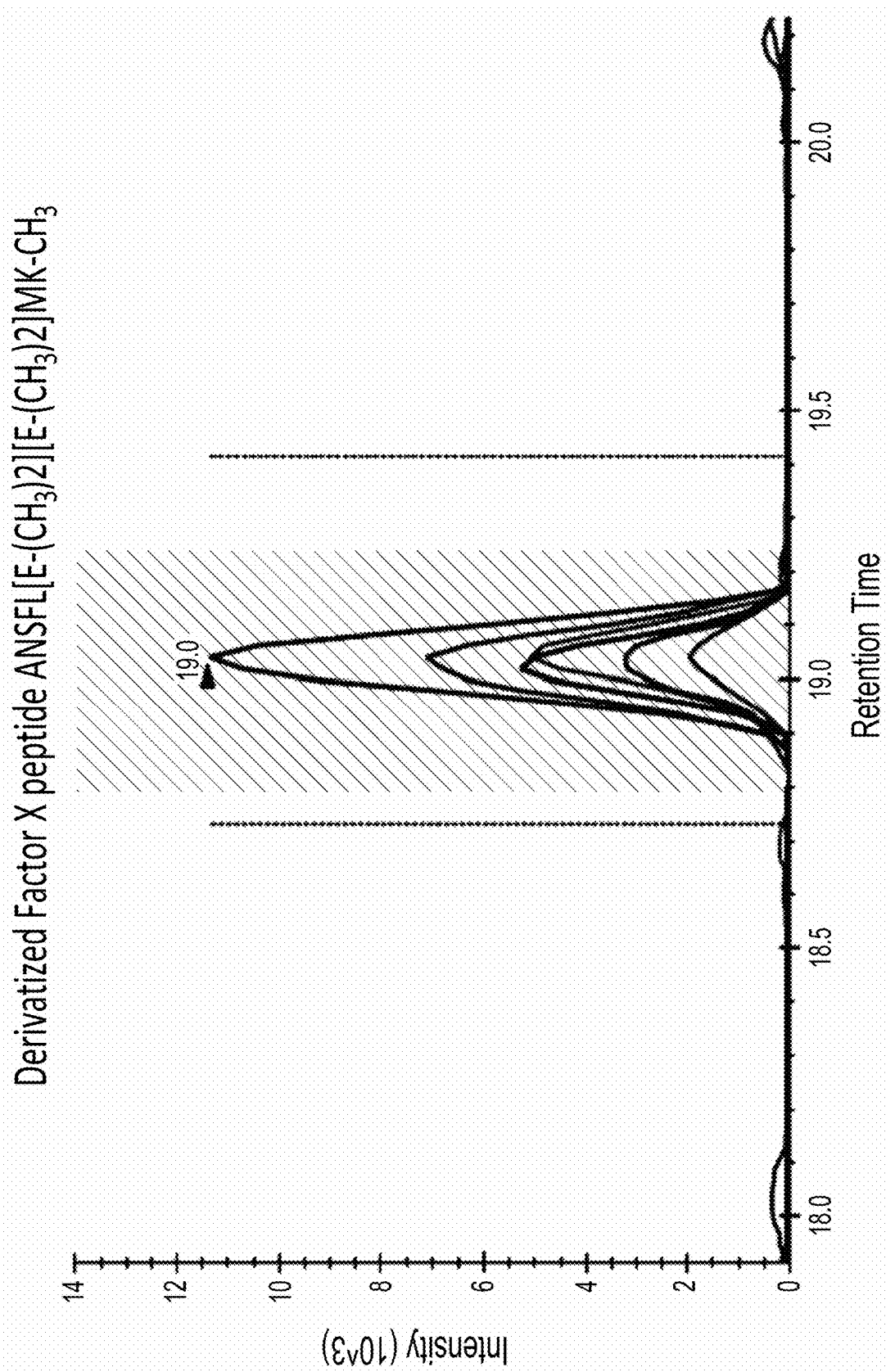
FIG. 3B shows the liquid chromatographic profile of the derivatized ANSFL[E-

Derivatization results in a consequential LC-MS signal increase. Such a signal increase can be seen in the comparison of liquid chromatography chromatograms, as shown in FIGS. 3A and 3B, where FIG. 3A shows the liquid chromatography intensity of ANSFL[E][E]MK (SEQ ID NO: 1) and FIG. 3B shows the significantly increased liquid chromatography intensity corresponding to the methyl ester derivative ANSFL[E-$(CH_3)_2$][E-$CH_3)_2$]MK-$CH_3$(SEQ ID NO: 2).

Gla-region peptides were derivatized for peptides derived from Factor II, IX, X, Protein S, and Protein C by LC-MS. The representative increase in signal response for derivatized peptide for increasing quantities of sample analyzed (1, 2, and 3 μg) is shown in FIG. 4 for the Factor II Gla-region peptide ANTFL[E-$(CH_3)_2$][E-$(CH_3)_2$]VR-$CH_3$ (SEQ ID NO: 72) and ANTFL[(E-$CH_3)_2$][E-$(CH_3)_2$]VRK-$CH_3$ (SEQ ID NO: 73).

In contrast to the LC-MS signal detected for the derivatized peptides, underivatized peptides assessed were essentially undetectable in the LC-MS, with the exception of ANTFL[E][E]VRK (SEQ ID NO: 5), which was detectable without necessitating derivatization.

LC-MS/MS Assay

The LC-MS/MS method was performed on a SCIEX 6500 triple quadrupole mass spectrometer coupled to a Waters Acquity UPLC system. Chromatographic separation of the peptides was achieved using a reversed-phase HSS T3 C18 column (2.1×100 mm, 1.8μ particle size). Table 2 below shows the LC method gradient conditions and mass spectrometer parameters, which comprises a mobile phase containing 0.1% formic acid in water (A) and 0.1% formic acid in acetonitrile (B). Resulting data were acquired by Analyst 1.6 software and analyzed by Skyline software 4.1.

TABLE 2

Chromatographic conditions for separation of surrogate peptides.
LC gradient program
ACQUITY UPLC ® HSS T3 C18 column (2.1 × 100 mm, 1.8 μm)

| Time (min) | Flow Rate | A (Water with 0.1% formic acid, %) | B (Acetonitrile with 0.1% formic acid, %) |
|---|---|---|---|
| 0 | 0.3 | 97.0 | 3.0 |
| 4 | 0.3 | 97.0 | 3.0 |
| 8 | 0.3 | 87.0 | 13.0 |
| 18 | 0.3 | 70.0 | 30.0 |
| 20.5 | 0.3 | 65.0 | 35.0 |
| 21.1 | 0.3 | 40.0 | 60.0 |
| 23.1 | 0.3 | 20.0 | 80.0 |
| 23.2 | 0.3 | 97.0 | 3.0 |
| 27 | 0.3 | 97.0 | 3.0 |

MS Parameters: Ion mode: ESI + Ve; CUR: 30; CAD: 9; IonSpray Voltage: 5500; Temperature: 400

Liquid chromatography (LC) and multiple reaction monitoring (MRM) parameters for individual peptides was first optimized using the extracted peptides which resulted from proteolytic cleavage of purified human prothrombin. Multiple reaction monitoring (MRM) for analysis of surrogate peptides of prothrombin and human serum albumin utilized $^{13}$C and $^{15}$N labeled lysine (K) and arginine (R) residues, as indicated in Table 3. The heavy labeled peptides of the purified human prothrombin shown in Table 3 below were used as internal standards to confirm peptide identity by retention time and MS fragmentation matching. The internal standard also addresses the post-digestion variability in MS ionization and sample evaporation in the autosampler.

TABLE 3

Multiple reaction monitoring (MRM) parameters for analysis of surrogate peptides of prothrombin and human serum albumin.

| Protein | Peptide | Peptide labeling | Parent Ion | Daughter Ion | DP | CE |
|---|---|---|---|---|---|---|
| Prothrombin (non-Gla peptides used for total prothrombin quantification) | SGIEC(CAM)QLWR. + 2y6.light (SEQ ID NO: 74) | light | 574.779 | 891.414 | 73 | 29.5 |
| | SGIEC(CAM)QLWR. + 2y5.light (SEQ ID NO: 74) | | 574.779 | 762.372 | 73 | 29.5 |
| | SGIEC(CAM)QLWR. + 2y4.light (SEQ ID NO: 74) | | 574.779 | 602.341 | 73 | 29.5 |
| | SGIEC(CAM)QLWR. + 2y3.light (SEQ ID NO: 74) | | 574.779 | 474.282 | 73 | 29.5 |
| | SGIEC(CAM)QLWR. + 2y6.heavy (SEQ ID NO: 74) | heavy | 579.784 | 901.422 | 73 | 29.5 |
| | SGIEC(CAM)QLWR. + 2y5.heavy (SEQ ID NO: 74) | | 579.784 | 772.38 | 73 | 29.5 |
| | SGIEC(CAM)QLWR. + 2y4.heavy (SEQ ID NO: 74) | | 579.784 | 612.349 | 73 | 29.5 |
| | SGIEC(CAM)QLWR. + 2y3.heavy (SEQ ID NO: 74) | | 579.784 | 484.291 | 73 | 29.5 |
| | TATSEYQTFFNPR. + 2y8.light (SEQ ID NO: 48) | light | 781.368 | 1072.521 | 88.1 | 37 |
| | TATSEYQTFFNPR. + 2y7.light (SEQ ID NO: 48) | | 781.368 | 909.458 | 88.1 | 37 |
| | TATSEYQTFFNPR. + 2y5.light (SEQ ID NO: 48) | | 781.368 | 680.352 | 88.1 | 37 |
| | TATSEYQTFFNPR. + 2y4.light (SEQ ID NO: 48) | | 781.368 | 533.283 | 88.1 | 37 |
| | TATSEYQTFFNPR. + 2y8.heavy (SEQ ID NO: 48) | heavy | 786.372 | 1082.529 | 88.1 | 37 |
| | TATSEYQTFFNPR. + 2y7.heavy (SEQ ID NO: 48) | | 786.372 | 919.466 | 88.1 | 37 |
| | TATSEYQTFFNPR. + 2y5.heavy (SEQ ID NO: 48) | | 786.372 | 690.36 | 88.1 | 37 |
| | TATSEYQTFFNPR. + 2y4.heavy (SEQ ID NO: 48) | | 786.372 | 543.291 | 88.1 | 37 |
| | ELLESYIDGR. + 2y8.light (SEQ ID NO: 49) | light | 597.804 | 952.473 | 74.7 | 30 |
| | ELLESYIDGR. + 2y7.light (SEQ ID NO: 49) | | 597.804 | 839.389 | 74.7 | 30 |
| | ELLESYIDGR. + 2y6.light (SEQ ID NO: 49) | | 597.804 | 710.347 | 74.7 | 30 |
| | ELLESYIDGR. + 2y5.light (SEQ ID NO: 49) | | 597.804 | 623.315 | 74.7 | 30 |

TABLE 3-continued

Multiple reaction monitoring (MRM) parameters for analysis of surrogate peptides of prothrombin and human serum albumin.

| Protein | Peptide | Peptide labeling | Parent Ion | Daughter Ion | DP | CE |
|---|---|---|---|---|---|---|
| | ELLESYIDGR. + 2y8.heavy (SEQ ID NO: 49) | heavy | 602.808 | 962.482 | 74.7 | 30 |
| | ELLESYIDGR. + 2y7.heavy (SEQ ID NO: 49) | | 602.808 | 849.398 | 74.7 | 30 |
| | ELLESYIDGR. + 2y6.heavy (SEQ ID NO: 49) | | 602.808 | 720.355 | 74.7 | 30 |
| | ELLESYIDGR. + 2y5.heavy (SEQ ID NO: 49) | | 602.808 | 633.323 | 74.7 | 30 |
| Carboxy-Prothrombin (Gla peptides used for quntification of fully carboxy prothrombin) | ANTFL[E][E]VRK_light_M + 2H-CO2 (SEQ ID NO: 5) | light | 647.817 | 625.817 | 100 | 21 |
| | ANTFL[E][E]VRK_light_M + 2H-2CO2 (SEQ ID NO: 5) | | 647.817 | 603.817 | 100 | 27 |
| | ANTFL[E][E]VRK_light_M + 2H-2CO2-H2O (SEQ ID NO: 5) | | 647.817 | 594.7 | 100 | 29 |
| | ANTFL[E][E]VRK_light_y6-2CO2 (SEQ ID NO: 5) | | 647.817 | 773.431 | 100 | 37 |
| | ANTFL[E][E]VRK_light_y5-2CO2 (SEQ ID NO: 5) | | 647.817 | 660.347 | 100 | 35 |
| | ANTFL[E][E]VRK_heavy_M + 2H-CO2 (SEQ ID NO: 5) | heavy | 651.82 | 629.779 | 100 | 21 |
| | ANTFL[E][E]VRK_heavy_M + 2H-2CO2 (SEQ ID NO: 5) | | 651.82 | 607.786 | 100 | 27 |
| | ANTFL[E][E]VRK_heavy_M + 2H-2CO2-H2O (SEQ ID NO: 5) | | 651.82 | 598.7 | 100 | 29 |
| | ANTFL[E][E]VRK_heavy_y6-2CO2 (SEQ ID NO: 5) | | 651.82 | 781.402 | 100 | 37 |
| | ANTFL[E][E]VRK_heavy_y5-2CO2 (SEQ ID NO: 5) | | 651.82 | 668.326 | 100 | 35 |
| MonoCarboxy-Prothrombin (Gla) | ANTFLE[E]VRK_light_M + 2H-CO2 (SEQ ID NO: 4) | light | 625.822 | 603.822 | 90 | 25 |
| | ANTFLE[E]VRK_light_M + 2H-CO2-H2O (SEQ ID NO: 4) | | 625.822 | 594.8 | 90 | 29 |
| | ANTFLE[E]VRK_light_y7-CO2 (SEQ ID NO: 4) | | 625.822 | 920.5 | 90 | 35 |
| | ANTFLE[E]VRK_light_y6-CO2 (SEQ ID NO: 4) | | 625.822 | 773.441 | 90 | 35 |
| | ANTFLE[E]VRK_light_y5-CO2 (SEQ ID NO: 4) | | 625.822 | 660.357 | 90 | 35 |
| | ANTFLE[E]VRK_heavy_M + 2H-CO2 (SEQ ID NO: 4) | heavy | 629.822 | 607.782 | 90 | 25 |
| | ANTFLE[E]VRK_heavy_M + 2H-CO2-H2O (SEQ ID NO: 4) | | 629.822 | 598.8 | 90 | 29 |
| | ANTFLE[E]VRK_heavy_y7-CO2 (SEQ ID NO: 4) | | 629.822 | 928.52 | 90 | 35 |
| | ANTFLE[E]VRK_heavy_y6-CO2 (SEQ ID NO: 4) | | 629.822 | 781.45 | 90 | 35 |
| | ANTFLE[E]VRK_heavy_y5-CO2 (SEQ ID NO: 4) | | 629.822 | 668.37 | 90 | 35 |
| Des-Carboxy-Prothrombin (descarboxy Gla peptides as a result of warfarin treatment) | ANTFLEEVRK. + 2y6.light (SEQ ID NO: 3) | light | 603.828 | 773.452 | 100 | 35 |
| | ANTFLEEVRK. + 2y5.light (SEQ ID NO: 3) | | 603.828 | 660.367 | 100 | 35 |
| | ANTFLEEVRK. + 2y6.heavy (SEQ ID NO: 3) | heavy | 607.835 | 781.466 | 100 | 35 |
| | ANTFLEEVRK. + 2y5.heavy (SEQ ID NO: 3) | | 607.835 | 668.382 | 100 | 35 |
| | GNLER. + 2y3.light (SEQ ID NO: 6) | light | 294.659 | 417.246 | 40 | 15 |
| | GNLER. + 2y2.light (SEQ ID NO: 6) | | 294.659 | 304.162 | 40 | 15 |
| | GNLER. + 2b2.light (SEQ ID NO: 6) | | 294.659 | 172 | 40 | 15 |
| | GNLER. + 2y3.heavy (SEQ ID NO: 6) | heavy | 299.663 | 427.254 | 40 | 15 |
| | GNLER. + 2y2.heavy (SEQ ID NO: 6) | | 299.663 | 314.17 | 40 | 15 |
| | GNLER. + 2b2.heavy (SEQ ID NO: 6) | | 299.663 | 172 | 40 | 15 |

TABLE 3-continued

Multiple reaction monitoring (MRM) parameters for analysis of surrogate peptides of prothrombin and human serum albumin.

| Protein | Peptide | Peptide labeling | Parent Ion | Daughter Ion | DP | CE |
|---|---|---|---|---|---|---|
| Human Serum Albumin | VFDEFKPLVEEPQNLIK 1 (SEQ ID NO: 75) | light | 682.4 | 712.4 | 88 | 29 |
| | VFDEFKPLVEEPQNLIK 2 (SEQ ID NO: 75) | | 682.4 | 970.5 | 88 | 29 |
| | VFDEFKPLVEEPQNLIK heavy 1 (SEQ ID NO: 75) | heavy | 685.1 | 720.4 | 89 | 29 |
| | VFDEFKPLVEEPQNLIK heavy 2 (SEQ ID NO: 75) | | 685.1 | 978.5 | 89 | 29 |
| | LVNEVTEFAK 1 (SEQ ID NO: 76) | light | 575.3 | 694.4 | 70 | 30 |
| | LVNEVTEFAK 2 (SEQ ID NO: 76) | | 575.3 | 595.3 | 70 | 30 |
| | LVNEVTEFAK heavy 1 (SEQ ID NO: 76) | heavy | 579.3 | 702.4 | 71 | 30 |
| | LVNEVTEFAK heavy 2 (SEQ ID NO: 76) | | 579.3 | 603.3 | 71 | 30 |

K and R in bold were labeled as $^{13}$C and $^{15}$N.
DP = declustering potential.
CE = collision energy.
CAM = carbamidomethyl.
Both DP and CE are mass spectrometric parameters optimized for individual peptides.

In a typical LC-MS/MS assay, derivatized peptides were used to assess the quantities of γ-carboxy peptides and γ-carboxy peptide proteoforms. The des-carboxy peptides and non-Gla peptides analyzed were obtained from a retained aliquot (20 μL) of the trypsin digest (proteolytic cleavage) sample which did not undergo the derivatization procedure.

The derivatized or underivatized peptide samples were placed in an LC-MS vial and analyzed by LC-MS/MS. For example, the γ-carboxy peptide ANTFL[E][E]VRK (SEQ ID NO: 5) and des-carboxy peptide GNLER (SEQ ID NO: 6) from the prothrombin Gla region, and peptides SGIECQLWR (SEQ ID NO: 47), TATSEYQTFFNPR (SEQ ID NO: 48), and ELLESTIDGR (SEQ ID NO: 77) of the non-Gla region were selected as surrogates for active/inactive and total prothrombin, respectively.

To quantify each of the γ-carboxylated prothrombin proteins, γ-carboxylated prothrombin protein proteoforms, and des-carboxylated prothrombin proteins, the optimized LC method was used to separate the individual γ-carboxy, γ-carboxy proteoforms, and des-carboxy peptides. The method resulted in resolution between fully γ-carboxylated ANTFL[E][E]VRK (SEQ ID NO: 5), mono-γ-carboxylated ANTFLE[E]VRK (SEQ ID NO: 4), and completely des-carboxylated ANTFLEEVRK (SEQ ID NO: 3) peptides, with retention times of 14.3, 12.5, and 13.0 min respectively, confirmed by the retention time of standard synthetic peptides. FIG. 1 demonstrates a selection of the Gla-region peptide sequences analyzed.

The fully γ-carboxylated ANTFL[E][E]VRK (SEQ ID NO: 5), mono-γ-carboxylated ANTFLE[E]VRK (SEQ ID NO: 4), and completely des-carboxylated ANTFLEEVRK (SEQ ID NO: 3) peptides were then subjected to tandem mass spectrometry analysis (LC-MS/MS) following the liquid chromatography separation. FIG. 5A shows the MS/MS spectrum of the des-carboxy peptide ANTFLEEVRK (SEQ ID NO: 3) with parent ion at m/z 607.8386 and γ-ions as the dominant fragments. FIG. 5B shows the MS/MS spectrum of the γ-carboxylated peptide ANTFLE[E]VRK (SEQ ID NO: 4) with parent ion having m/z 629.8301 and ions with one $CO_2$ loss (γ-$CO_2$) as the dominant fragments. FIG. 5C shows the MS/MS spectrum of the γ-carboxylated ANTFL[E][E]VRK (SEQ ID NO: 5) peptide with the parent ion at m/z 651.7717 and ions corresponding to two $CO_2$ losses (γ-2$CO_2$) as the dominant fragments.

The LC-MS/MS assay was validated for linearity, precision, accuracy, and recovery. Linearity of the assay was assessed by adding in different concentrations of the unlabeled prothrombin standard (2.5-100 μg/ml) into human serum albumin. The data for calibration curves in human serum albumin and human serum were linear, having an $r^2$ value of 0.97 and 0.98 respectively, as shown in FIG. 6A and FIG. 6B, respectively. The linearity of the data in FIG. 6A indicates that the peptide response correlates with the concentration in human serum albumin. The linearity of the data in FIG. 6B indicates that the peptide response correlates with the concentration in human serum. Accuracy and extraction recovery were assessed by adding aliquots of standard prothrombin at two concentrations (40 and 80 μg/ml) into pooled human plasma from control adults, as shown in FIG. 6C.

Inter-day precision of the assay was performed with the plasma samples processed on three different days. Prothrombin time for INR determination was measured using a STA-Compact coagulation analyzer (Diagnostica Stago). The published (UW Laboratory Medicine) prothrombin time and INR reference range in individuals with normal coagulation is 10.7-15.6 sec and 0.8-1.3, respectively. The value of a therapeutic INR varies with the underlying medical condition; e.g., INR=2-3 for stroke prevention in individuals with atrial fibrillation. The INR is derived from prothrombin time (PT), which is calculated as a ratio of the patient's PT to a control PT, and standardized for the potency of the thromboplastin reagent developed by the World Health Organization (WHO) using the following formula:

INR=Patient PT÷Control PT

LC-MS/MS Assay Quantification of γ-Carboxy and Des-Carboxy Peptides

The abundance of γ-carboxylated proteins, γ-carboxylated protein proteoforms, and des-carboxylated proteins, as well as total prothrombin, was determined in serum samples from control and warfarin-treated individuals by determining the quantities of the γ-carboxylated peptide ANTFL[E][E]VRK (SEQ ID NO: 5), the γ-carboxylated peptide proteoform ANTFLE[E]VRK (SEQ ID NO: 4), and the des-carboxylated peptides ANTFLEEVRK (SEQ ID NO: 3) and GNLER (SEQ ID NO: 6). The absolute abundance of γ-carboxy peptide ANTFL[E][E]VRK (SEQ ID NO: 5) was determined in serum samples from control and warfarin-treated individuals by a calibration curve prepared by adding unlabeled prothrombin into human plasma. Similarly, the abundance of des-carboxy peptides ANTFLEEVRK (SEQ ID NO: 3) and GNLER (SEQ ID NO: 6) was determined in serum samples from control and warfarin-treated individuals. The relative abundance of the γ-carboxy peptide proteoform ANTFLE[E]VRK (SEQ ID NO: 4) was determined in serum samples from control and warfarin-treated individuals.

Absolute or relative protein abundance (pmol/g) across healthy control and warfarin-treated adults (Group 1) and control adults (Group 2) were then compared by the Kruskal-Wallis test followed by a Mann-Whitney test.

FIGS. 7A-7D show a comparison of the abundance of total prothrombin, γ-carboxylated peptide ANTFL[E][E]VRK (SEQ ID NO: 5), des-carboxy peptide GNLER (SEQ ID NO: 6), and des-carboxy peptide ANTFLEEVRK (SEQ ID NO: 3), respectively, in serum samples from control and warfarin-treated individuals. Each dot and square in FIGS. 7A-7D represents the individual subjects from the control and warfarin-treated groups, respectively. Error bars indicate the standard deviation. FIGS. 7A and 7B demonstrate the significant reduction in the observed levels of total prothrombin (p=0.02) and γ-carboxylated prothrombin (p<0.0001) in warfarin-treated subjects compared to control subjects. Des-carboxylated prothrombin was significantly (p<0.0001) elevated in warfarin-treated subjects, as seen in FIG. 7C and FIG. 7D, as well as FIG. 8B. Des-carboxy peptide ANTFLEEVRK (SEQ ID NO: 3) is a low response peptide.

Additionally, the method described above has been used to detect peptides from Factor IX in control and warfarin-treated adults, as seen in FIG. 9A, Factor X in control and warfarin-treated adults, as seen in FIG. 9B, Protein S in control and warfarin-treated adults, as seen in FIG. 9C, Factor VII in control and warfarin-treated adults, as seen in FIG. 9D, Protein C in control and warfarin-treated adults, as seen in FIG. 9E, and Protein Z in control and warfarin-treated adults, as seen in FIG. 9F.

INR Value Determination

Associations between different peptide/protein INR were evaluated by linear regression. The protein abundance data are presented as mean±SD. Prothrombin time was measured in citrated whole blood using a STA-Compact coagulation analyzer (Diagnostica Stago). INR was calculated from that measurement divided by a reference control prothrombin time, with adjustment for the sensitivity of the thromboplastin reagent that was used in the prothrombin time analysis.

FIGS. 10A-10D show the correlation between the INR values and each of the abundance of total prothrombin, carboxy peptide ANTFL[E][E]VRK (SEQ ID NO: 5), and des-carboxy peptides GNLER (SEQ ID NO: 6) and ANTFLEEVRK (SEQ ID NO: 3) in serum samples from a warfarin-treated subject (Group 1). The INR values negatively correlated with the carboxy peptides, while they positively correlated with the des-carboxy peptides. FIGS. 10E-10F show the correlation between the carboxy peptide ANTFL[E][E]VRK (SEQ ID NO: 5) with des-carboxy peptides GNLER (SEQ ID NO: 6) and ANTFLEEVRK (SEQ ID NO: 3) in the same sample set. There was a strong negative correlation between the carboxy peptide and des-carboxy peptides. This data indicates the method can quantify carboxylated peptides and des-carboxylated peptides simultaneously.

Administering Anticoagulant to a Patient

Drug selection and dose of an anticoagulant agent is determined by the clinical indication and patient attributes. For example, a typical starting dose of warfarin for prevention of stroke in patients with atrial fibrillation is 5-mg a day, with possible adjustments increasing or decreasing the amount of drug administered based on patient-specific factors such as age, race, concomitant medications (CYP2C9 inhibitors or inducers), concomitant disease (e.g., liver or kidney dysfunction) as well as genetic factors (e.g. altered function CYP2C9, VKORC1 and CYP4F2 variants). INR is generally measured 48 hours after initiation of warfarin therapy and the daily dose is further increased or decreased depending on the measured INR value and the target range. A therapeutic INR is ultimately achieved through an iterative process of INR measurement and dose adjustment.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for quantifying one or more of γ-carboxylated proteins, γ-carboxylated protein proteoforms, and des-carboxylated proteins in a biological sample, comprising:

(a) extracting a sample comprising one or more proteins selected from the group consisting of γ-carboxylated proteins, γ-carboxylated protein proteoforms, and des-carboxylated proteins from the biological sample with a solvent, wherein the sample is a protein precipitate and extracting the sample with the solvent provides a liquid extract and a residual protein precipitate, wherein the residual protein precipitate is enriched with the one or more proteins relative to the sample;

(b) separating the liquid extract from the residual protein precipitate;

(c) dissolving the residual protein precipitate in an aqueous medium to provide a solution comprising the one or more proteins;

(d) contacting the solution comprising the one or more proteins with a protease, to provide a solution of peptides comprising one or more of γ-carboxylated peptides, γ-carboxylated peptide proteoforms, and des-carboxylated peptides; and (e) determining the quantity of the one or more of γ-carboxylated peptides, γ-carboxylated peptide proteoforms, and des-carboxylated peptides in the solution of peptides.

2. The method of claim 1, wherein the one or more of γ-carboxylated proteins, γ-carboxylated protein proteoforms, and des-carboxylated proteins are derived from one or more vitamin K-dependent blood clotting factors.

3. The method of claim 1, wherein determining the quantity of the one or more of γ-carboxylated peptides, γ-carboxylated peptide proteoforms, and des-carboxylated peptides comprises mass spectrometric (MS) analysis.

4. The method of claim 3, wherein the mass spectrometric analysis comprises tandem mass spectrometric (MS/MS) analysis.

5. The method of claim 3, wherein the mass spectrometric analysis comprises liquid chromatographic mass spectrometric (LC-MS) analysis.

6. The method of claim 3, wherein the mass spectrometric analysis comprises multiple reaction monitoring of a fragmentation profile of each of the one or more of γ-carboxylated peptides, γ-carboxylated peptide proteoforms, and des-carboxylated peptides.

7. The method of claim 1, wherein the one or more of γ-carboxylated proteins, γ-carboxylated protein proteoforms, and des-carboxylated proteins are derived from prothrombin (Factor II), Factor VII, Factor IX, Factor X, the anticoagulant proteins C and S, the factor X-targeting protein Z, osteocalcin, the calcification-inhibiting matrix Gla protein (MGP), the growth arrest specific gene 6 protein (GAS6), periostin, transmembrane Gla proteins (TMGPs), transthyretin (thyroxin binding protein), and proline-rich Gla-proteins (PRGPs).

8. The method of claim 1, wherein the biological sample is plasma, serum, blood, or a dried blood spot.

9. The method of claim 8, wherein the plasma, serum, or blood has a volume of about 5 uL to about 100 uL.

10. The method of claim 2, wherein the one or more vitamin K-dependent blood clotting factors is prothrombin (Factor II).

11. The method of claim 1, wherein the protease is trypsin or chymotrypsin.

12. The method of claim 1, wherein the γ-carboxylated peptides comprise one or more peptide sequences,
wherein the peptide sequence for prothrombin comprises ANTFL[E][E]VRK (SEQ ID NO: 5) and GNL[E]R (SEQ ID NO: 7); Factor VII comprises ANAFL[E][E]LRPGSL[E]R (SEQ ID NO: 8), [E]IFKDA[E]R (SEQ ID NO: 9), and PGSL[E]R (SEQ ID NO: 51); Factor IX comprises L[E][E]FVQGNL[E]R (SEQ ID NO: 10), [E]CM[E][E]K (SEQ ID NO: 11), CSF[E][E]AR (SEQ ID NO: 12), [E]VF[E]NT[E]R (SEQ ID NO: 13) and TT[E]FWK (SEQ ID NO: 14); Factor X comprises ANSFL[E][E]MK (SEQ ID NO: 1), [E]VF[E]DSDK (SEQ ID NO: 15), TN[E]FWNK (SEQ ID NO: 16), and GHL[E]R (SEQ ID NO: 59); Protein S comprises ANSLL[E][E]TK (SEQ ID NO: 17), QGNL[E]R (SEQ ID NO: 18) and [E]CI[E][E]LCNK (SEQ ID NO: 19); Protein C comprises ANSFL[E][E]LR (SEQ ID NO: 20), HSSL[E]R (SEQ ID NO: 21), and [E]IFQNVDDTLAFWSK (SEQ ID NO: 22); osteocalcin comprises YLYQWLGAPVPYPDPL[E]PR (SEQ ID NO: 23) and [E]VC[E]LNPDCD[E]LADHIGFQ[E]AYR (SEQ ID NO: 24); and MGP comprises SKPVH[E]LNR (SEQ ID NO: 25) and [E]ACDDYR (SEQ ID NO: 26).

13. The method of claim 1, wherein the des-carboxylated peptides comprise one or more peptide sequences,
wherein the peptide sequence for prothrombin comprises ANTFLEEVRK (SEQ ID NO: 3) and GNLER (SEQ ID NO: 6); Factor VII comprises ANAFLEELRPGSLER (SEQ ID NO: 27), EIFKDAER (SEQ ID NO: 28), and PGSLER (SEQ ID NO: 53); Factor IX comprises LEEFVQGNLER (SEQ ID NO: 29), ECMEEK (SEQ ID NO: 30), CSFEEAR (SEQ ID NO: 31), EVFENTER (SEQ ID NO: 32) and TTEFWK (SEQ ID NO: 33); Factor X comprises ANSFLEEMK (SEQ ID NO: 34), EVFEDSDK (SEQ ID NO: 35), TNEFWNK (SEQ ID NO: 36), and GHLER (SEQ ID NO: 60); Protein S comprises ANSLLEETK (SEQ ID NO: 37), QGNLER (SEQ ID NO: 38), and ECIEELCNK (SEQ ID NO: 39); Protein C comprises ANSFLEELR (SEQ ID NO: 40), HSSLER (SEQ ID NO: 41), and EIFQNVDDTLAFWSK (SEQ ID NO: 42); osteocalcin comprises YLYQWLGAPVPYPDPLEPR (SEQ ID NO: 43) and EVCELNPDCDELADHIGFQEAYR (SEQ ID NO: 44); and MGP comprises SKPVHELNR (SEQ ID NO: 45) and EACDDYR (SEQ ID NO: 46).

14. The method of claim 1, wherein the γ-carboxylated peptide proteoforms comprise one or more peptide sequences, wherein at least one glutamate or glutamic acid residue is γ-carboxylated, and wherein fewer than all glutamate or glutamic acid residues are γ-carboxylated.

15. The method of claim 1, wherein the liquid extract comprises an albumin.

\* \* \* \* \*